United States Patent
Chen et al.

(10) Patent No.: US 12,318,255 B2
(45) Date of Patent: Jun. 3, 2025

(54) METHODS FOR PREDICTING THE RISK OF OBSTRUCTIVE SLEEP APNEA

(71) Applicant: AMCAD BIOMED CORPORATION, Taipei (TW)

(72) Inventors: Argon Chen, Taipei (TW); Yi-li Lee, Taipei (TW); Pei-Yu Chao, Taipei (TW); Wei-Hao Chen, Taipei (TW); Wei-Yu Hsu, Taipei (TW)

(73) Assignee: AmCad BioMed Corporation, Taipei (TW)

( * ) Notice: Subject to any disclaimer, the term of this patent is extended or adjusted under 35 U.S.C. 154(b) by 140 days.

(21) Appl. No.: 18/198,785

(22) Filed: May 17, 2023

(65) Prior Publication Data

US 2024/0130714 A1 Apr. 25, 2024
US 2024/0225609 A9 Jul. 11, 2024

Related U.S. Application Data

(60) Provisional application No. 63/418,702, filed on Oct. 24, 2022.

(51) Int. Cl.
*A61B 8/00* (2006.01)
*A61B 8/08* (2006.01)
*G06N 20/00* (2019.01)

(52) U.S. Cl.
CPC ............ *A61B 8/5223* (2013.01); *A61B 8/08* (2013.01); *A61B 8/40* (2013.01); *A61B 8/469* (2013.01); *G06N 20/00* (2019.01)

(58) Field of Classification Search
CPC .......... A61B 8/5223; A61B 8/08; A61B 8/40; A61B 8/469; G06N 20/00
See application file for complete search history.

(56) References Cited

U.S. PATENT DOCUMENTS

| | | | |
|---|---|---|---|
| 2013/0289401 A1* | 10/2013 | Colbaugh | A61B 5/395 600/536 |
| 2018/0027077 A1* | 1/2018 | Melodia | G16H 40/67 370/254 |
| 2020/0238107 A1* | 7/2020 | Shabtay | A61K 31/506 |
| 2021/0374399 A1* | 12/2021 | Cheung | G06V 40/50 |
| 2023/0172486 A1* | 6/2023 | Shouldice | A61B 5/1079 600/301 |
| 2024/0024597 A1* | 1/2024 | Dos Santos | A61M 16/0666 |

(Continued)

OTHER PUBLICATIONS

Mohammad et al.; "Detection of Airway Occlusion in Simulated Obstructive Sleep Apnea/Hypopnea using Ultrasound: an In Vitro Study"; 32nd Annual International Conference of the IEEE EMBS Buenos Aires, Argentina, Aug. 31-Sep. 4, 2010; pp. 284-287 (Year: 2010).*

(Continued)

*Primary Examiner* — Dixomara Vargas
(74) *Attorney, Agent, or Firm* — Birch, Stewart, Kolasch & Birch, LLP

(57) ABSTRACT

Disclosed are computer-implemented or computer-aided method for diagnosing or predicting the risk of obstructive sleep apnea in a subject. The methods comprise determining whether the subject has obstructive sleep apnea based on at least one quantitative ultrasound parameter and/or at least one morphometric parameter.

19 Claims, 16 Drawing Sheets
(2 of 16 Drawing Sheet(s) Filed in Color)

(56) References Cited

U.S. PATENT DOCUMENTS

2024/0181185 A1* 6/2024 Fox ..................... A61M 16/205

OTHER PUBLICATIONS

Amal et al.; "Ultrasonographic Detection of Airway Obstruction in a Model of Obstructive Sleep Apnea"; Ultrasound Int Open 2017; 3 : E34-E42 (Year: 2017).*

Mohanna; "Feasibility of air-coupled ultrasound and rebound tonometry techniques to evaluate mechanical properties of soft tissues related to obstructive sleep apnea"; Medical Physics University of Eastern Finland Faculty of Science and Forestry (Year: 2021).*

Dioguardi et al.; "Quantification of hepatic steatosis with ultrasound: promising role of attenuation imaging coefficient in a biopsy-proven cohort" European Radiology (2020) 30:2293-2301 (Year: 2020).*

* cited by examiner

| Logistic Regression (Forward Method) | BUI Value [B1] | BUI Value [A2] | BUI Value [A1] | BMI | Age | AUROC (moderate-severe OSA) |
|---|---|---|---|---|---|---|
| BMI < 25 | P = 0.0339 | — | P = 0.1228 | — | — | AUC = 0.830 |
| BMI ≥ 25 | — | P = 0.0087 | — | P = 0.0385 | P = 0.0212 | AUC = 0.873 |

(a)

(b)

METHODS FOR PREDICTING THE RISK OF OBSTRUCTIVE SLEEP APNEA

CROSS REFERENCE

This Non-provisional application claims the priority under 35 U.S.C. § 119(e) on U.S. Patent Provisional Application No. 63/418,702 filed on Oct. 24, 2022, the entire contents of which are hereby incorporated by reference.

TECHNOLOGY FIELD

The present invention relates to computer-implemented or computer-aided methods of diagnosing obstructive sleep apnea. The present invention also relates to a method for computer-aided diagnosis of obstructive sleep apnea in a subject.

BACKGROUND OF THE INVENTION

Upper airway collapse in obstructive sleep apnea (OSA) occurs due to the variation between the transmural pressure and the longitudinal tension of the pharyngeal airway. This can be attributed to either a discrepancy between facial skeletal morphology and upper airway soft tissue (including the volume of lymphoid tissues), or aberrant neuromuscular function resulting in laxity of airway muscles. To date, studies evaluating the impact of OSA on upper airway tissue in a non-invasive and reproducible way are lacking.

Globally, over a billion individuals are diagnosed with OSA. In the US, this chronic condition affects 38% of the population, yet recent studies show that over 80% of the population remain undiagnosed. This may be contributed by difficulty getting approval for sleep studies, alongside reduced awareness of this chronic condition. There remains strong associations between chronic OSA and systemic hypertension (HTN), heart failure (HF), atrial fibrillation (AF), and coronary heart disease (CHD), cerebrovascular strokes and overall mortality. Management of OSA mitigates resistant cardiovascular diseases such as recalcitrant hypertension.

Polysomnography (PSG) is the gold standard diagnostic tool for OSA. Diagnosis and severity are classified using the apnea-hypopnea index (AHI) according to the American Academy of Sleep Medicine (AASM). However, PSG does not provide easy interpretation of upper airway muscle collapse, and the levels of obstruction. For treatment of OSA, knowing the site and the dynamics behind airway collapse has shown promise in optimizing outcome. Nonetheless, phenotyping airway collapsibility and its impact on OSA remains a challenge. Significant limitations remain despite different imaging modalities that have been used for airway phenotyping.

Biomedical ultrasound is cost-effective, non-invasive, and radiation-free, which already sets it apart favorably from better studied imaging modalities including computed tomography (CT) or magnetic resonance imaging (MRI) for OSA. Previous studies have shown qualitative sonographic data to correlate with OSA severity with good reliability (Liu K H et al., *Sleep.* 2007; 30(11):1503-1508). In certain fields of medicine, backscattered ultrasound imaging (BUI) has been used to overcome the need for traditional CT or MRI scanning (Wan Y L et al., *Proc Inst Mech Eng H.* 2015; 229(6):419-428; Guerrero Q W et al., *Ultrasound Med Biol.* 2019; 45(2):429-439; and Hosokawa A., *IEEE Trans Ultrason Ferroelectr Freq Control.* 2015; 62(6): 1201-1210).

SUMMARY OF THE INVENTION

The present invention is at least based on the finding that characteristics of tissue adjacent to airway of a subject assessed via ultrasound are indicative of obstructive sleep apnea (OSA) or the risk of OSA in said subject. Therefore, the present invention provides a method for diagnosing or predicting the risk of OSA in a subject. The method requires performing specific quantitative analysis on ultrasonic radio frequency data of the region of interest (i.e., a region corresponding to a tissue adjacent to airway), and then determining whether the subject is at risk of OSA based on the results of the quantitative analysis.

In particular, in one aspect, the present invention provides a computer-implemented method for predicting the risk of obstructive sleep apnea (OSA) in a subject, the method comprising:
  receiving ultrasonic radio-frequency data echoed from a region of interest in upper airway of the subject;
  determining at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and
  determining whether the subject is at risk of OSA based on the at least one quantitative ultrasound parameter, wherein a statistical value of the at least one quantitative ultrasound parameter higher or lower than a threshold is indicative of the risk of OSA in the subject.

In another aspect, the present invention provides a non-transitory computer-readable storage medium including instructions which, when executed, cause at least one processor to at least:
  receive ultrasonic radio frequency data of a region of interest in upper airway of a subject;
  determine at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and
  determine whether the subject is at risk of obstructive sleep apnea based on the at least one quantitative ultrasound parameter, wherein a statistical value of the at least one quantitative ultrasound parameter higher or lower than a threshold is indicative of the risk of obstructive sleep apnea in the subject.

According to the present invention, the region of interest includes a posterior portion of tongue of the subject.

In some embodiments, the threshold is determined based on corresponding at least one quantitative ultrasound parameter of one or more normal subjects. According to certain embodiments of the present invention, the threshold is determined using a machine learning model trained with data of the corresponding at least one quantitative ultrasound parameter of one or more normal individuals and data of corresponding at least one quantitative ultrasound parameter of one or more patients confirmed as having obstructive sleep apnea.

In a further aspect, the present invention provides a method for computer-aided diagnosis or risk assessment of obstructive sleep apnea (OSA) in a subject, the method comprising:
  positioning the subject with respect to an automatic ultrasonic scanning system;

scanning, with the automatic ultrasonic scanning system, a location corresponding to upper airway of the subject, to obtain ultrasonic radio frequency data;

receiving, with at least one processor, ultrasonic radio frequency data of a region of interest in upper airway of a subject;

determining, with the at least one processor, at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and determining, with the at least one processor, whether the subject is at risk of obstructive sleep apnea based on the at least one quantitative ultrasound parameter, wherein a statistical value of the at least one quantitative ultrasound parameter higher or lower than a threshold is indicative of the risk of obstructive sleep apnea in the subject.

In some embodiments, the subject is positioned by laser alignment, aligning head and neck of the subject to a sagittal plane, a Frankfort horizontal plane (FH plane), and a cross-sectional plane through the Hyoid bone and the external acoustic Meatus (HM plane) of the subject. More specifically, the head and neck of the subject are positioned in supine position and then positioned to the center with the FH plane perpendicular to the horizon, with an ultrasound transducer of the automatic ultrasonic scanning system aligned with the HM plane to perform transverse cross-sectional ultrasonic scan.

According to the present invention, the region of interest includes a posterior portion of tongue of the subject.

In some embodiments, the threshold is determined based on corresponding at least one quantitative ultrasound parameter of one or more normal subjects. According to certain embodiments of the present invention, the threshold is determined using a machine learning model trained with data of the corresponding at least one quantitative ultrasound parameter of one or more normal individuals and data of corresponding at least one quantitative ultrasound parameter of one or more patients confirmed as having obstructive sleep apnea.

The present invention also provides a system configured to perform the above-described methods for computer-aided diagnosis of obstructive sleep apnea (OSA) in a subject.

In a still further aspect, the present invention provides a method for computer-aided diagnosis of obstructive sleep apnea in a subject, the method comprising:

positioning the subject with respect to an automatic ultrasonic scanning system, wherein the subject is positioned by laser alignment, aligning head and neck of the subject to a sagittal plane, a Frankfort horizontal plane (FH plane), and a cross-sectional plane through the Hyoid bone and the external acoustic Meatus (HM plane) of the subject, and wherein the head and neck of the subject are positioned in supine position and positioned to the center with the FH plane perpendicular to the horizon, with an ultrasound transducer of the automatic ultrasonic scanning system aligned with the HM plane to perform transverse cross-sectional ultrasonic scan, or with an ultrasound transducer of the automatic ultrasonic scanning system aligned parallel to the sagittal plane to perform sagittal ultrasonic scan;

the automatic ultrasonic scanning system obtaining at least one transverse ultrasound image of upper airway of the subject, or at least one sagittal ultrasonic image of upper airway of the subject;

receiving, with at least one processor, the at least one transverse ultrasound image or the at least one sagittal ultrasonic image;

determining, with the at least one processor, at least one morphometric parameter based on the at least one transverse ultrasound image or at least one sagittal ultrasonic image; and determining, with the at least one processor, whether the subject is at risk of obstructive sleep apnea based on the at least one morphometric parameter, wherein a statistical value of the at least one morphometric parameter higher or lower than a threshold is indicative of the risk of obstructive sleep apnea in the subject.

In some embodiments, the automatic ultrasonic scanning system automatically moves the ultrasound transducer to perform a sector scan covering the HM plane, to obtain the at least one transverse ultrasound image, which is a sequence of transverse ultrasound images.

In some embodiments, the sector scan covers about 0 to about 15 degrees below and about 0 to about 15 degrees above the HM plane.

In some embodiments, the threshold is determined based on corresponding at least one morphometric parameters of one or more normal individuals.

In some embodiments, the threshold is determined using a machine learning model trained with data of the corresponding at least one morphometric parameter of one or more normal individuals and data of corresponding at least one morphometric parameter of one or more patients confirmed as having obstructive sleep apnea.

In some embodiments, the at least one morphometric parameter is determined using a trained machine learning model based on the at least one transverse ultrasound image or the at least one sagittal ultrasonic image.

In another aspect, the present invention provides a system configured to perform the above-described methods for computer-aided diagnosis of obstructive sleep apnea (OSA) in a subject, based on the at least one morphometric parameter.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

Figure 1:
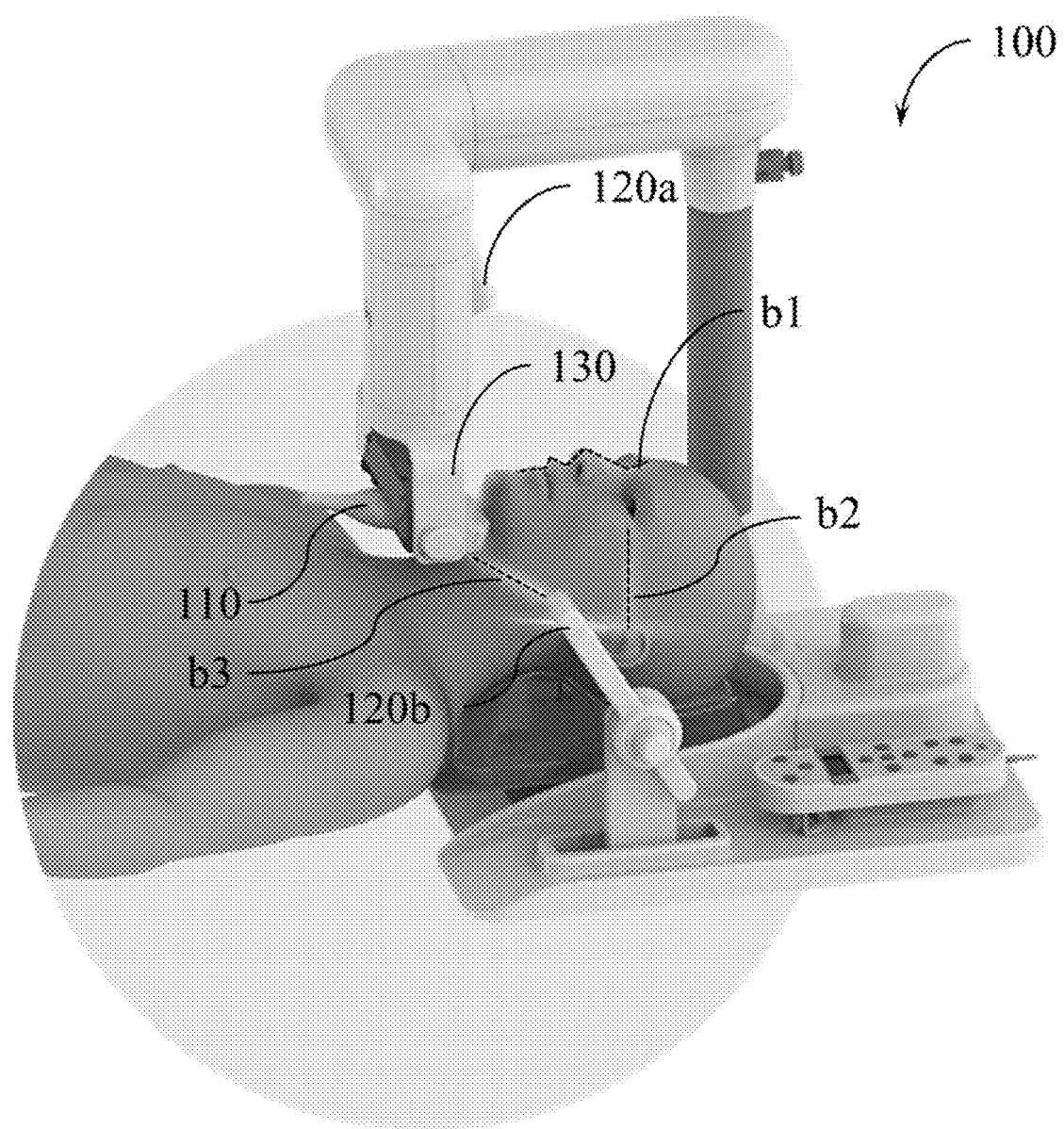
Figure 2A:
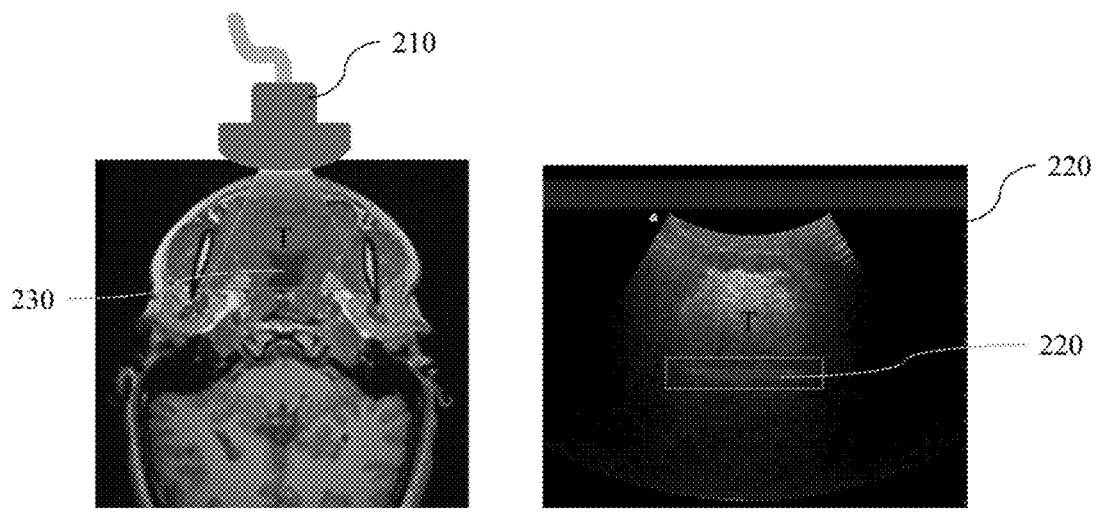

FIG. 1 illustrates a standardized submental ultrasound scan with laser alignment FIG. 2A shows ultrasound transducer positioning of a submental ultrasound scan of a subject and a corresponding transverse ultrasound image. In the left of FIG. 2A is an MRI image of an HM cross-sectional plane (cross-sectional plane through the Hyoid bone and the external acoustic Meatus) of the subject. In the right is the corresponding transverse ultrasound image obtained. The tongue region is annotated with "T" and the tissue-airspace interface is marked with a rectangle.

Figure 2B:
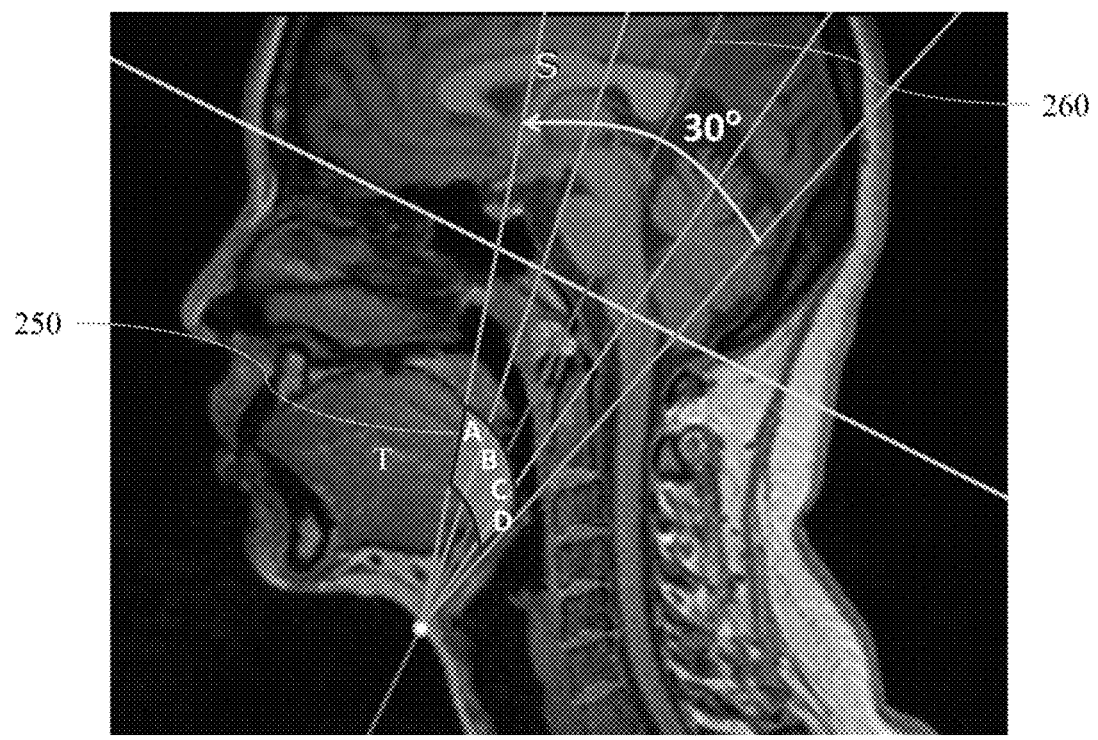

FIG. 2B shows an MRI image of a sagittal plane of the subject, illustrating a 30-degree sector region of upper airway swept by an automatic scan and the regions of interest to be analyzed with quantitative ultrasound parameter(s).

Figure 2C:
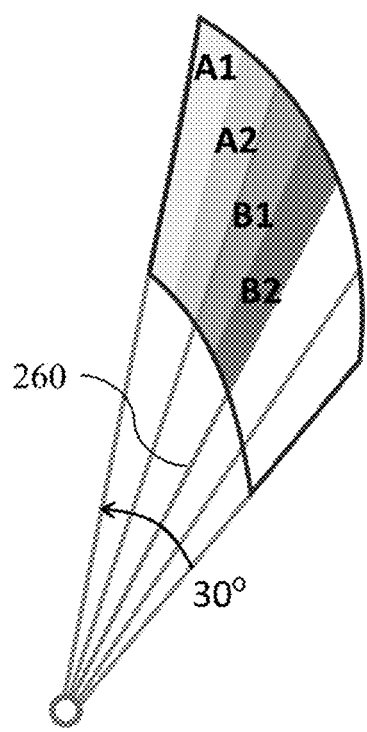

FIG. 2C shows relative position of four sub-regions where each covers a 3.75-degree sector region.

Figure 3:
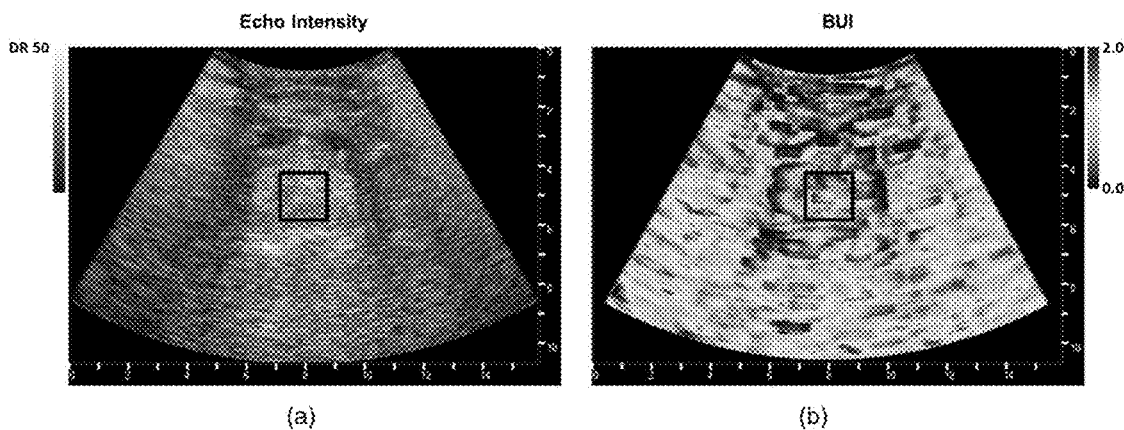
Figure 3:
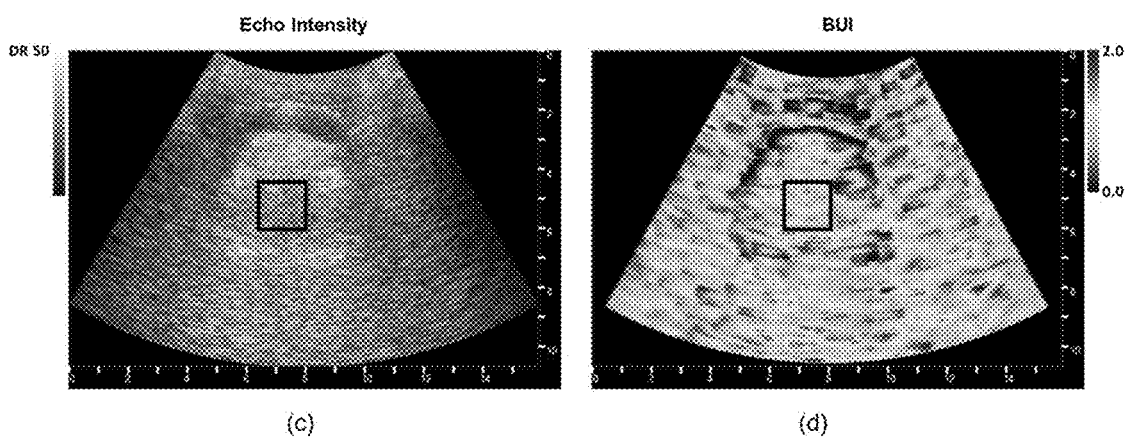

FIG. 3 shows B-mode (log-compressed echo intensity) images (a, c), and backscattered ultrasound imaging (BUI) color maps (b, d) constituted of the Nakagami parameter values computed from sliding window. The black square indicates the region of interest (ROI) for echo intensity measurement and BUI analysis. Images were acquired and computed from B region of mild obstructive sleep apnea (OSA) (a, b) and moderate OSA patient (c, d).

Figure 4:
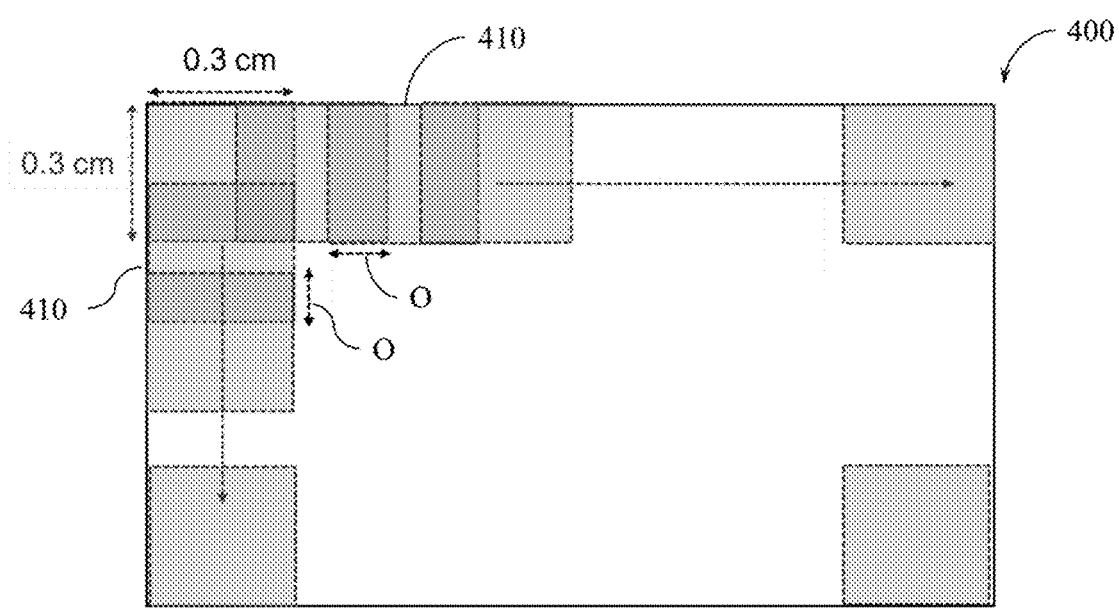

FIG. 4 illustrates sliding widows for the calculation of Nakagami parameter values.

Figure 5:
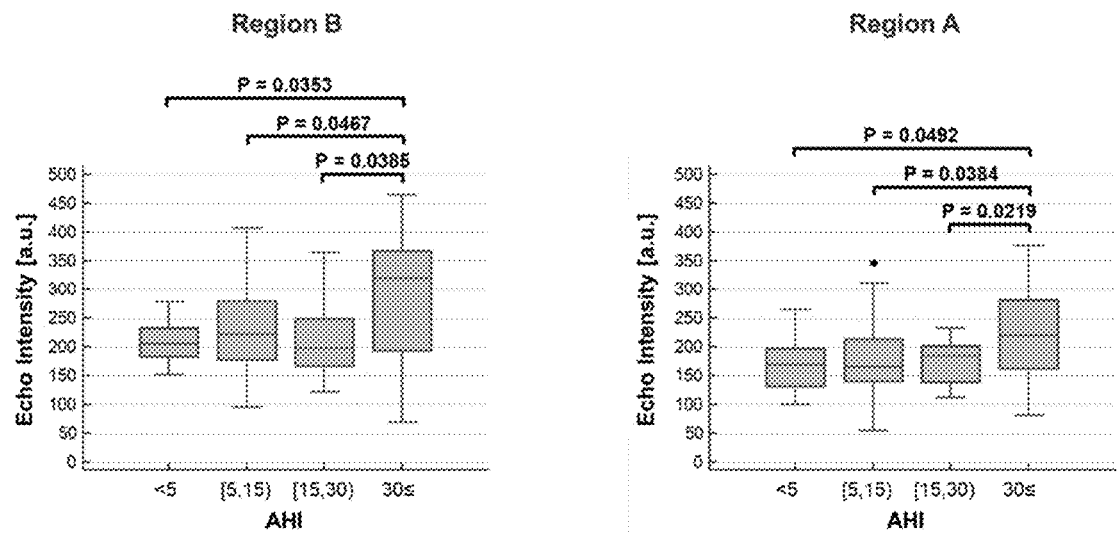

FIG. 5 shows the results of statistical analysis of echo intensity measurements of the four severity groups for B and A regions.

Figure 6:
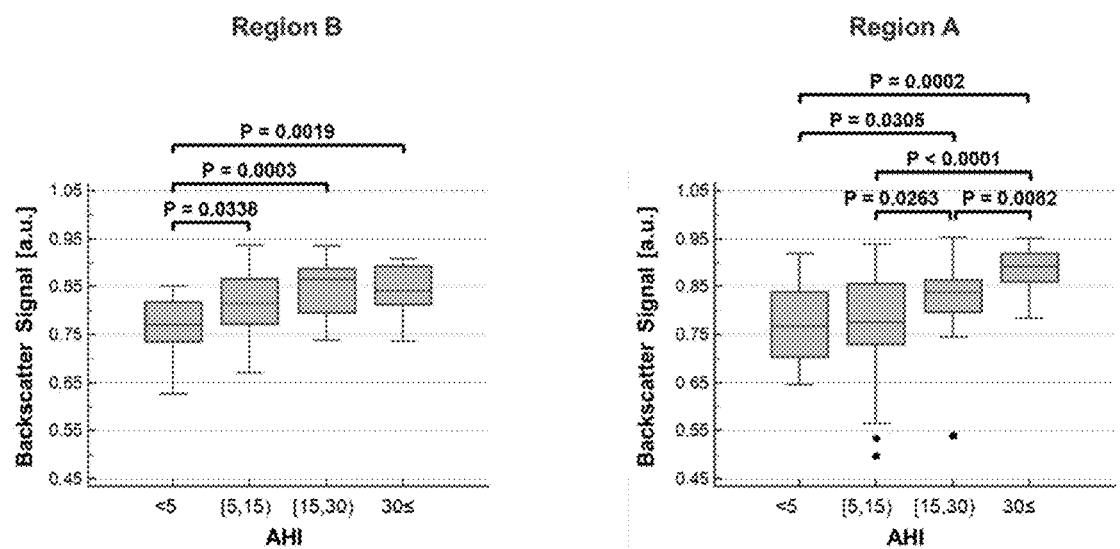

FIG. 6 shows the results of statistical analysis of BUI measurements of the four severity groups for B and A regions.

Figure 7:
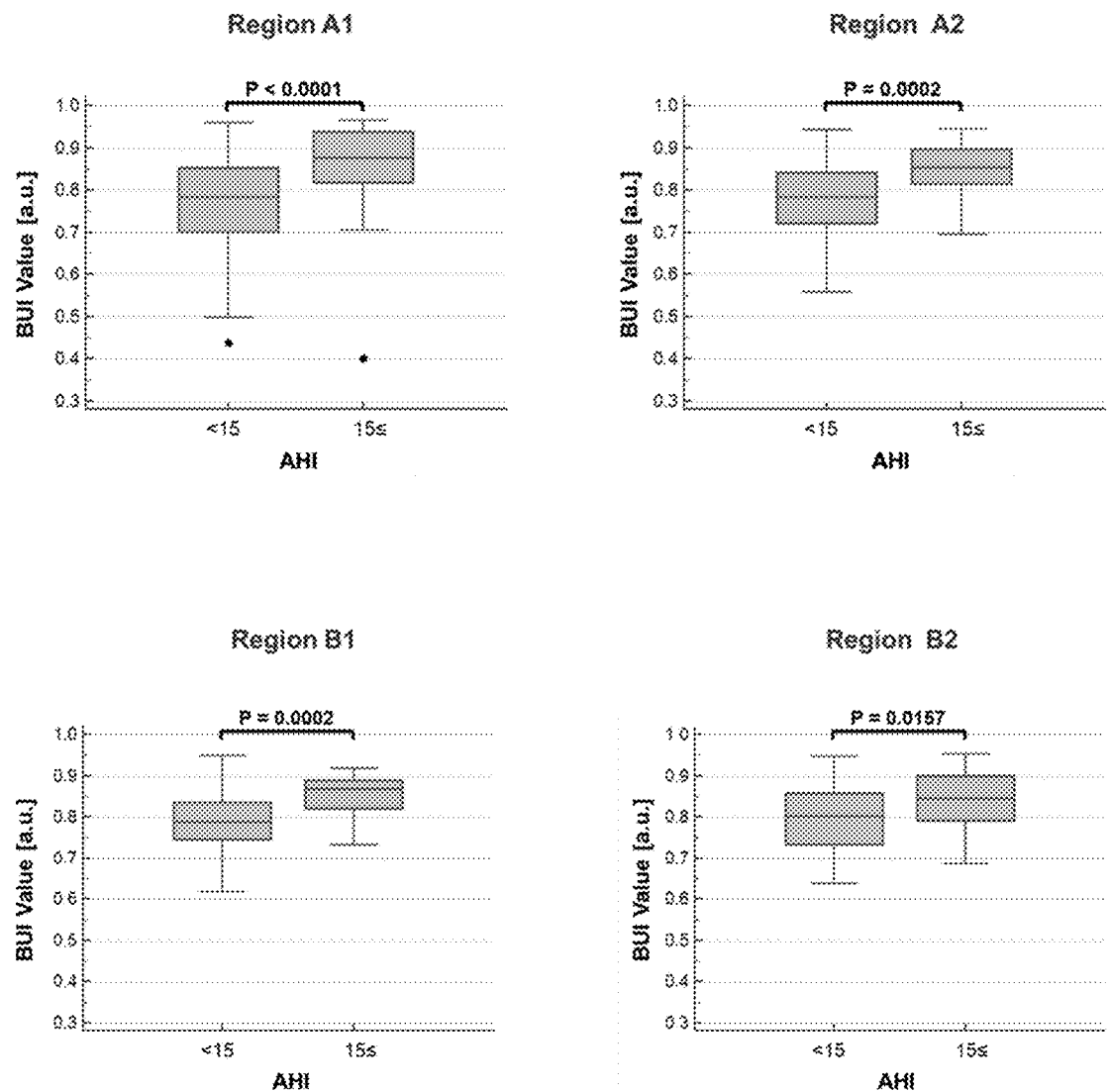

FIG. 7 shows comparisons of BUI measurements for no or mild OSA and moderate-to-severe OSA in the four sub-regions A1, A2, B1 and B2.

Figure 8:
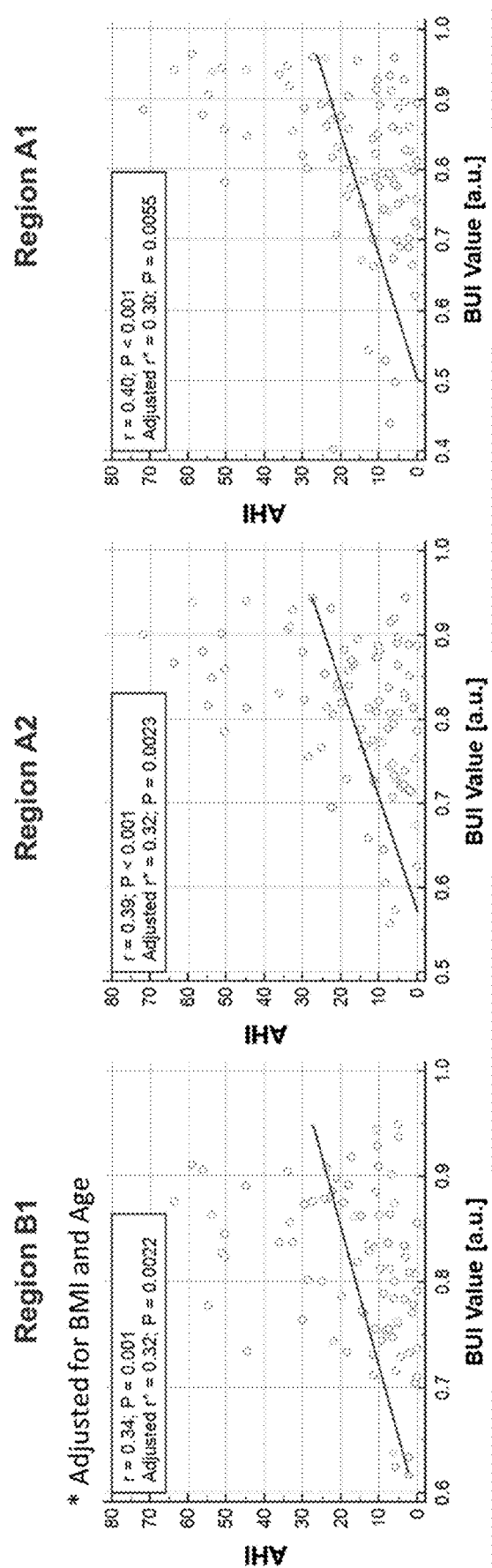

FIG. 8 shows correlation of BUI measurements from posterior of tongue (genioglossus muscle) in three sub-regions with the AHI. * denotes partial correlation after controlling for BMI and age.

Figure 9:
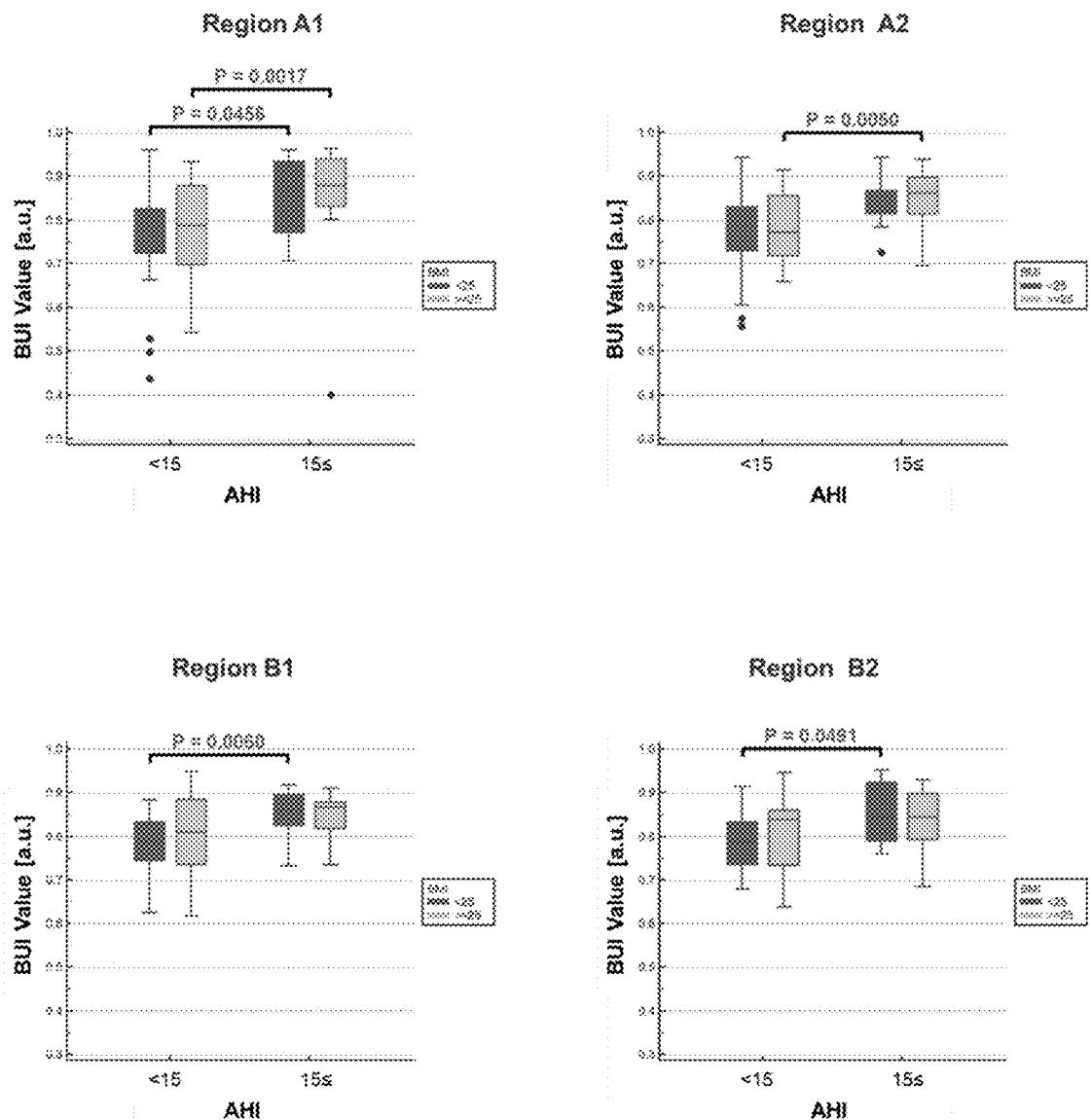

FIG. 9 shows comparisons of BUI measurements for no or mild OSA and moderate-severe OSA, stratified into normal and overweight-obese subgroups, in the four sub-regions A1, A2, B1 and B2.

Figure 10:
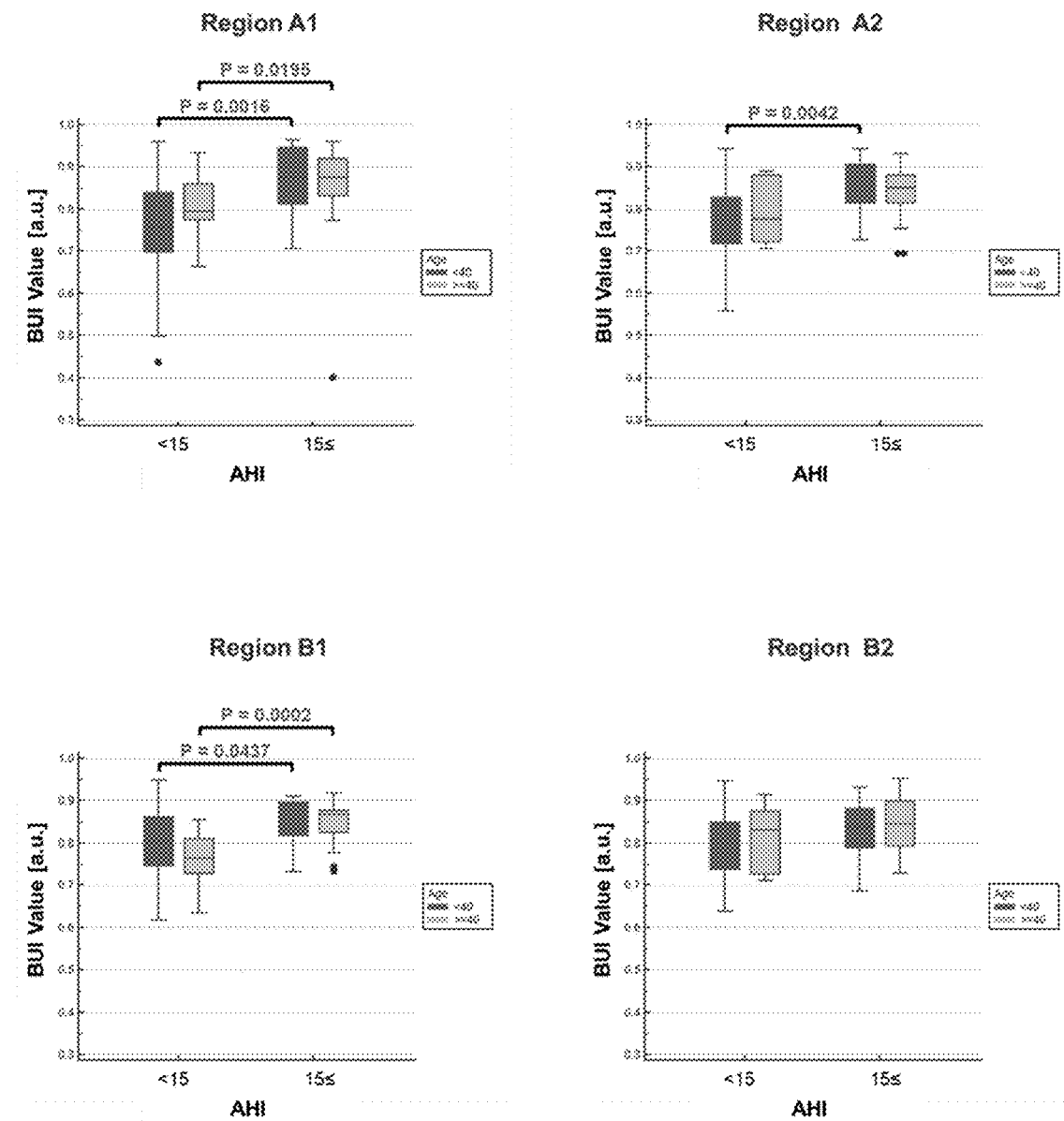

FIG. 10 shows comparisons of BUI measurements for no or mild OSA and moderate-severe OSA, stratified into Age<40 and Age≥40 subgroups, in the four sub-regions A1, A2, B1 and B2.

Figure 11:
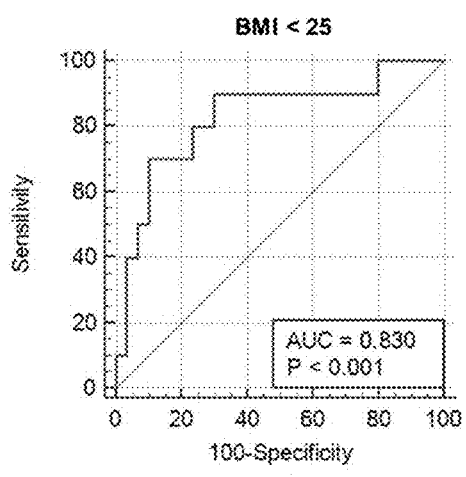
Figure 11:
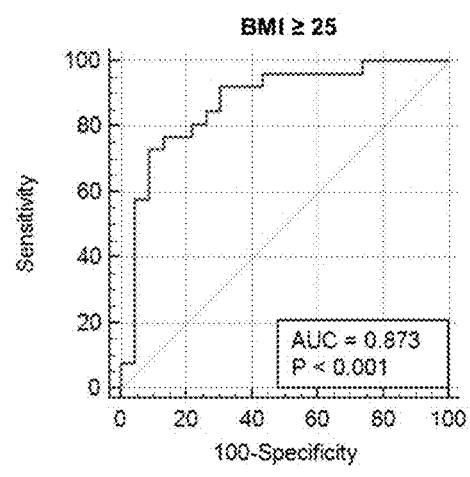

FIG. 11 shows receiver operating characteristic (ROC) curves for probability of moderate-severe OSA in the (a) normal BMI, and (b) overweight-obese subgroup.

Figure 12:
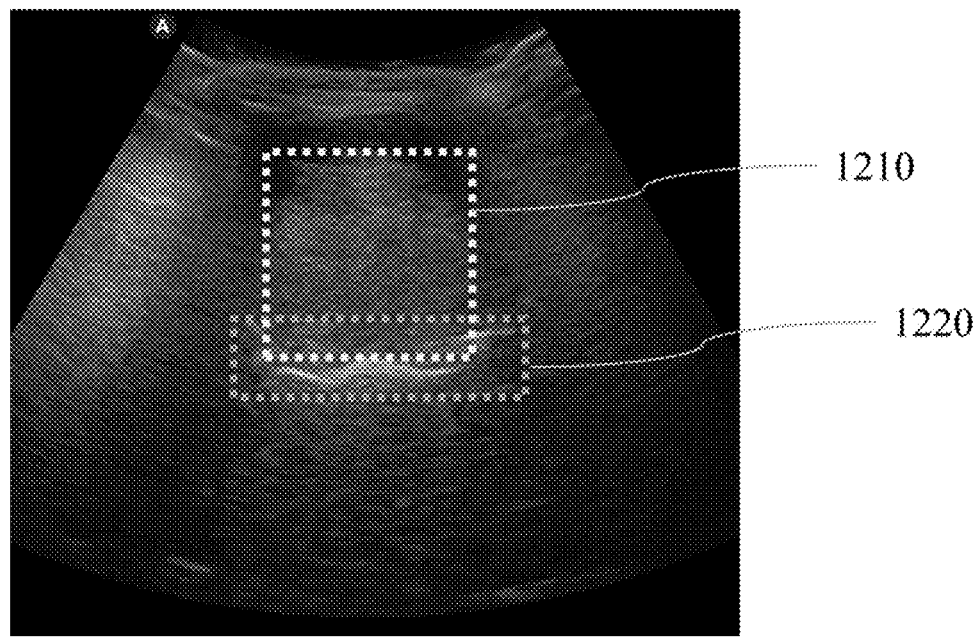

FIG. 12 illustrates a process of determining a region of interest based on a B-mode image.

Figure 13:
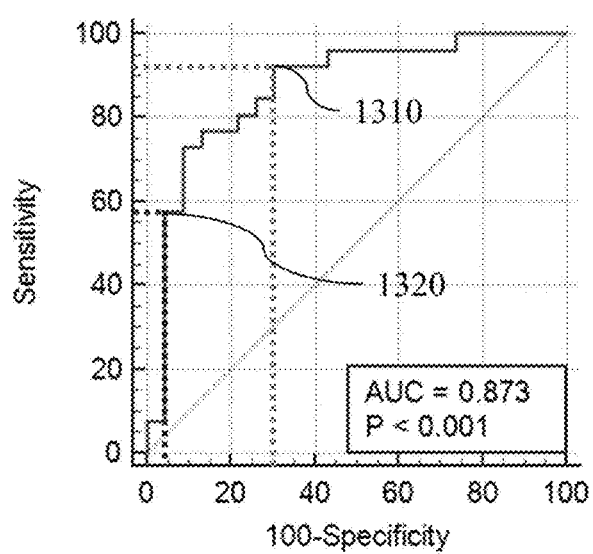

FIG. 13 illustrates an exemplary determination of threshold based on an AUROC curve.

Figure 14A:
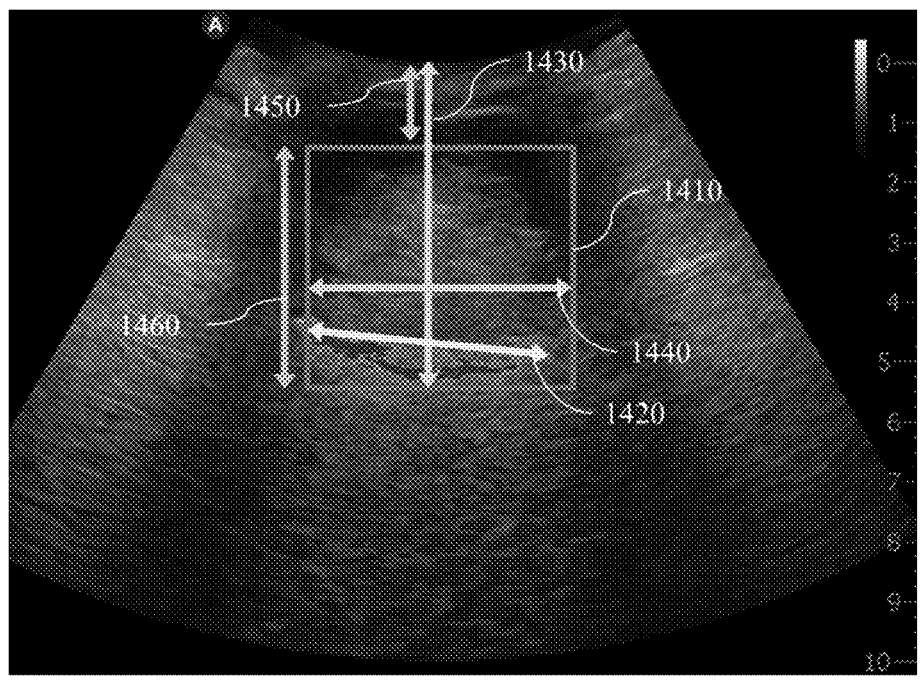

FIG. 14A shows a typical ultrasound B-mode image obtained in region C, which is a transverse view of the superficial tissue, tongue and the tissue-airway interface, wherein the morphometric measurements are marked. 1410: tissue. 1420: airway width. 1430: antero-posterior location (depth) of the airspace. 1440: tongue width. 1450: superficial tissue thickness. 1460: deep tissue thickness.

Figure 14B:
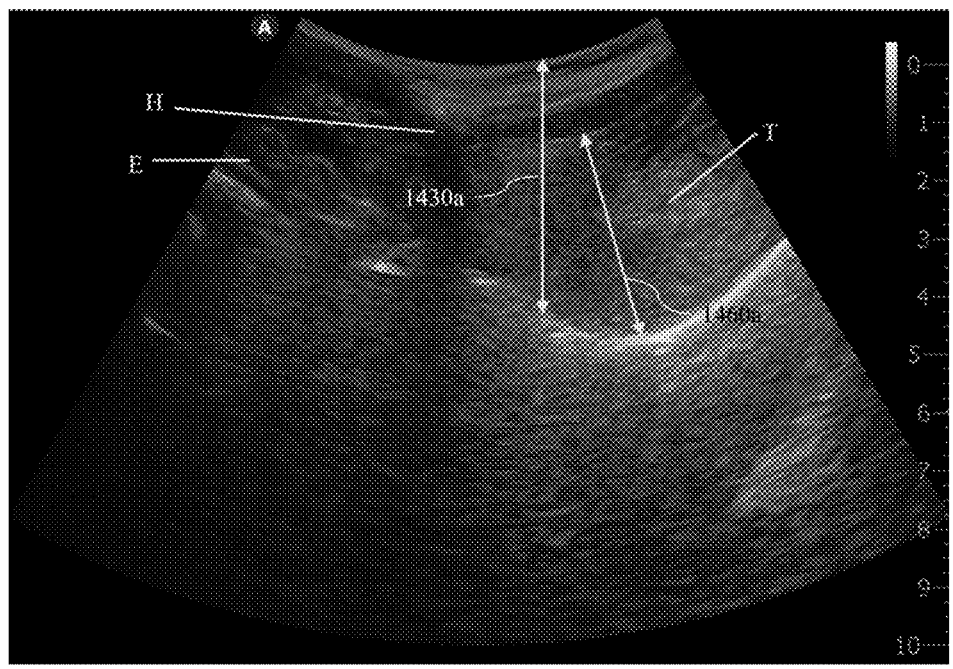

FIG. 14B shows a typical ultrasound B-mode image, which is a sagittal view of the superficial tissue, tongue and the tissue-airway interface, wherein the morphometric measurements are marked. 1430a: antero-posterior location (depth) of the airspace. 1460a: deep tissue (tongue) thickness. T: tongue. H: hyoid bone. E: epiglottis.

Figure 15:
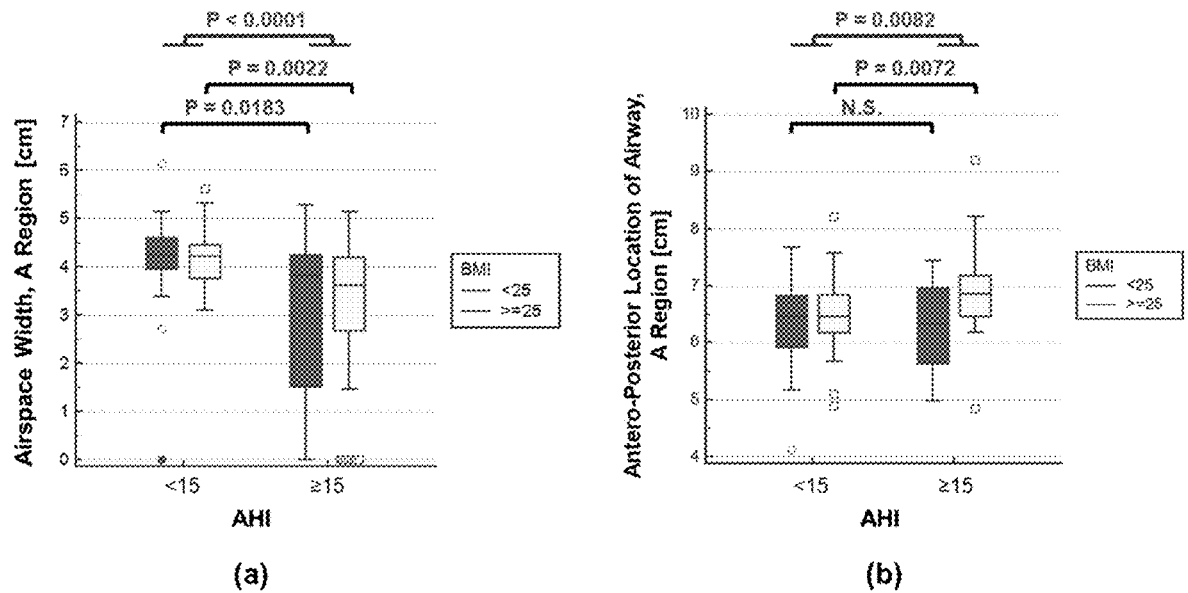

FIG. 15 shows the comparisons of the (a) width and (b) antero-posterior location (depth) of the airspace for region A.

Figure 16:
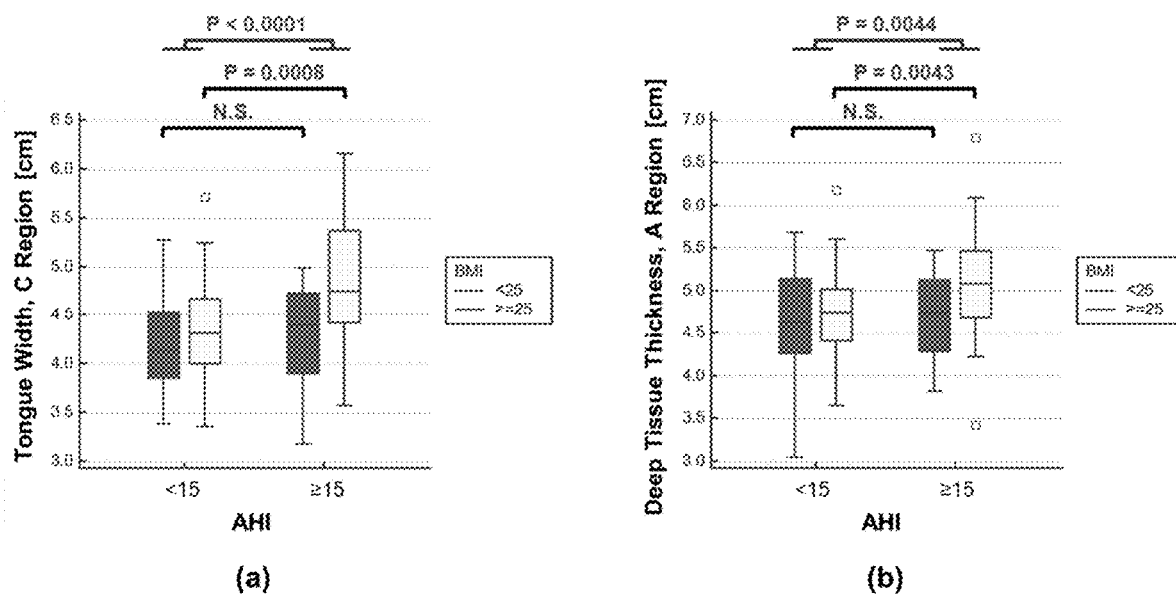

FIG. 16 shows the comparison of the tongue width at region C and the comparison of the deep tissue thickness at region A.

Figure 17:
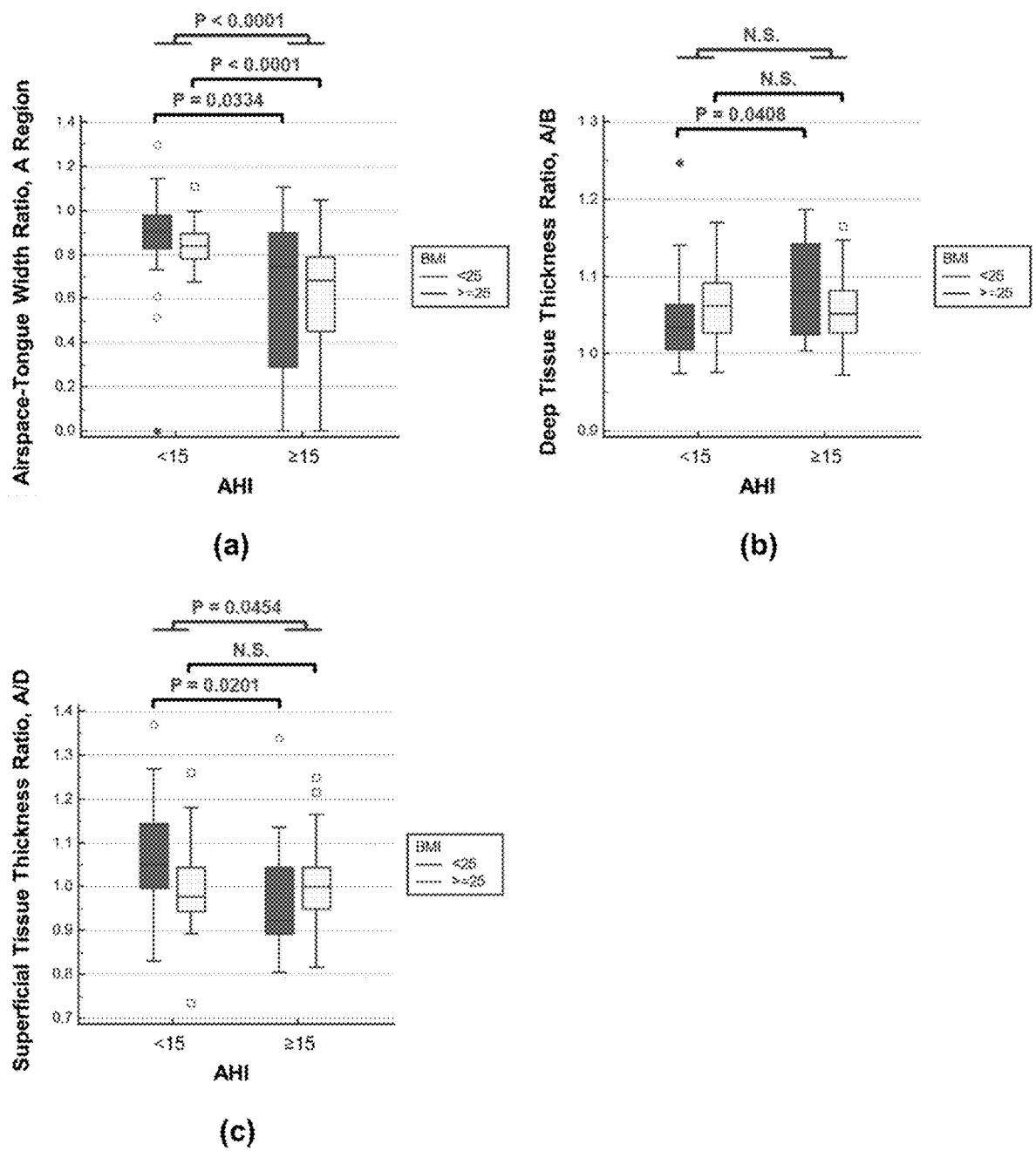

FIG. 17 shows comparison of the (a) airspace-tongue width ratio measured in region A, (b) ratio of deep tissue thickness measured in region A and B, and (c) ratio of superficial tissue thickness measured in region A and D for no-to-mild and moderate-to-severe OSA stratified into normal and overweight-obese subgroups.

Figure 18:
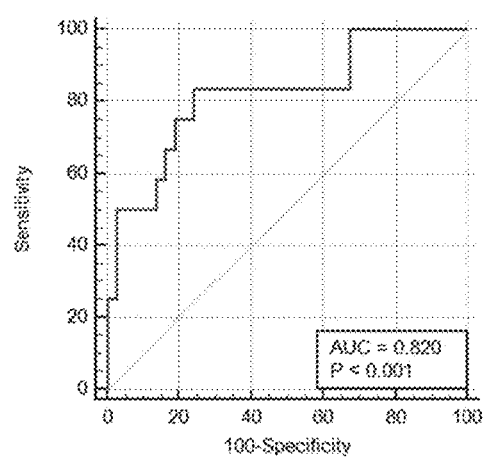
Figure 18:
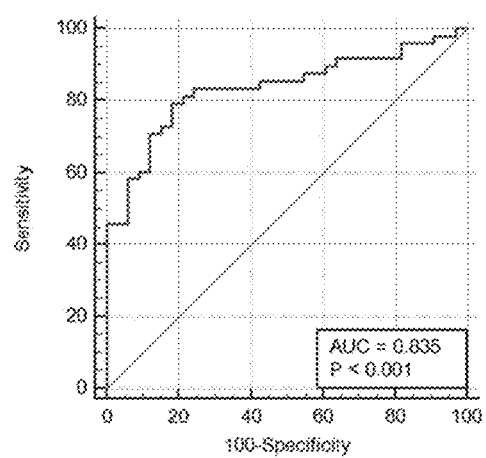

FIG. 18 shows receiver operating characteristic (ROC) curves for probability of moderate-severe OSA in the (a) normal BMI, and (b) overweight-obese subgroup

DETAILED DESCRIPTION OF THE INVENTION

The following description is merely intended to illustrate various embodiments of the invention. As such, specific embodiments or modifications discussed herein are not to be construed as limitations to the scope of the invention. It will be apparent to one skilled in the art that various changes or equivalents may be made without departing from the scope of the invention.

In order to provide a clear and ready understanding of the present invention, certain terms are first defined. Additional definitions are set forth throughout the detailed description. Unless defined otherwise, all technical and scientific terms used herein have the same meanings as is commonly understood by one of skill in the art to which this invention belongs.

As used herein, the singular forms "a", "an", and "the" include plural referents unless the context clearly dictates otherwise. Thus, for example, reference to "a component" includes a plurality of such components and equivalents thereof known to those skilled in the art.

As used herein, the term "comprise" or "comprising" is generally used in the sense of include/including which means permitting the presence of one or more features, ingredients or components. The term "comprise" or "comprising" encompasses the term "consists" or "consisting of."

As used herein, the term "about" or "approximately" refers to a degree of acceptable deviation that will be understood by persons of ordinary skill in the art, which may vary to some extent depending on the context in which it is used. In general, "about" or "approximately" may mean a numeric value having a range of ±10% around the cited value.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

As used herein, the terms "subject," "individual" and "patient" refer to any mammalian subject for whom diagnosis, prognosis, treatment, or therapy is desired, particularly humans. Other subjects may include cattle, dogs, cats, guinea pigs, rabbits, rats, mice, horses, and so on.

The term "a normal individual" as used herein may be used to refer to an individual who is basically in a healthy condition without particular diseases (e.g., obstructive sleep apnea), and may refer to a single normal/healthy individual or a group of normal/healthy individuals.

As used herein, the term "obstructive sleep apnea" or the abbreviation "OSA" refers to a sleep disorder that is caused by complete or partial obstruction of a subject's airway, leading to repetitive episodes of shallow or paused breathing during sleep, despite the subject's effort to breathe. In some embodiments, obstructive sleep apnea (OSA) refers to a breathing disorder that occurs primarily during sleep with consequences that may persist throughout the waking hours in the form of sleepiness.

The term "apnea-hypopnea index" or "AHI" as used herein means as the number of apnea events plus the number of hypopnea events per hour.

As used herein, a patient with "no obstructive sleep apnea (OSA)" or "without obstructive sleep apnea (OSA)" refers to a patient with an AHI fewer than five events per hour; a patient with "mild obstructive sleep apnea" or "mild OSA" refers to a patient with an AHI of five or more events per hour but fewer than 15 events per hour; a patient with "moderate obstructive sleep apnea" or "moderate OSA" refers to a patient with an AHI of 15 or more events per hour but fewer than 30 events per hour; and a patient with "severe obstructive sleep apnea" or "severe OSA" refers to a patient with an AHI of 30 or more events per hour.

An objective of the present invention is to differentiate patients with no or mild OSA from patients with moderate-to-severe OSA, and this objective is achieved by analyzing at least one quantitative ultrasound parameter within a region of interest corresponding to a tissue adjacent to the patient's airway. Therefore, in some embodiments, the risk of OSA refers to the risk of moderate-to-severe OSA.

The present invention provides in one aspect a computer-implemented method for predicting the risk of obstructive sleep apnea (OSA) in a subject, the method comprising:
  receiving or retrieving ultrasonic radio-frequency data of a region of interest in upper airway of the subject;
  determining at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and
  determining whether the subject is at risk of OSA based on the at least one quantitative ultrasound parameter, wherein a statistical value of the at least one quantitative ultrasound parameter higher or lower than a threshold is indicative of the risk of OSA in the subject.

According to the present invention, ultrasound scanning is performed over a location corresponding to upper airway of the subject to collect ultrasonic radio frequency data or to obtain ultrasound images. Preferably, the head and neck of the subject are positioned with respect to an ultrasound transducer of an automatic ultrasonic scanning system, and the scan is performed automatically, so as to accurately and repeatably obtain ultrasonic radio frequency data covering those of a region of interest. In some embodiments, the region of interest corresponds to a posterior portion of tongue of the subject.

In some embodiments, the method further comprising positioning the subject with respect to an automatic ultrasonic scanning system, wherein the subject is positioned by laser alignment, aligning head and neck of the subject to a (central) sagittal plane, a Frankfort horizontal plane (FH plane), and a cross-sectional plane through the Hyoid bone and the external acoustic Meatus (HM plane) of the subject, and wherein the head and neck of the subject are positioned in supine position and positioned to the center with the FH plane perpendicular to the horizon, with an ultrasound transducer of the automatic ultrasonic scanning system aligned with the HM plane to perform a submental transverse cross-sectional ultrasonic scan.

Specifically, to perform the submental transverse cross-sectional ultrasonic scan, the ultrasound transducer is directed to be aligned with the HM plane and the sagittal plane, such that an imaging plane of the ultrasound transducer is aligned with the HM plane and the imaging plane of the ultrasound transducer is perpendicular to the sagittal plane.

Some suitable positioning methods for head and neck assessment are described in US 2020/0352544 A1, the content of which is incorporated herein by reference in its entirety.

As used herein, "tissue adjacent to airway" refers to a soft tissue, preferably a muscle, in close proximity to, or directly connected to the pharyngeal airway of a subject. In some embodiments, the tissue adjacent to airway may be one of a number of muscles that surround the pharyngeal airway and influence its patency. In some embodiments, the tissue adjacent to airway is a palatal muscle, a tongue muscle, a pharyngeal muscle, or a hyoid muscle. The palatal muscle includes but is not limited to a palatoglossus muscle, a palatopharyngeus mucle, a levator veli palatini muscle, a tensor veli palatini muscle, and a musculus uvulae muscle. The tongue muscle includes but is not limited to a protruder muscle, a genioglossus muscle, a geniohyoid muscle, a retractor muscle, a hyoglossus muscle, a styloglossus muscle, and a palatoglossus muscle. The pharyngeal muscle includes but is not limited to a superior pharyngeal muscle, a middle pharyngeal muscle, an interior pharyngeal muscle, and a stylopharyngeus muscle. The hyoid muscle in includes but is not limited to a suprahyoid muscle, a mylohyoid muscle, a hyoglossus muscle, an anterior belly muscle, a posterior belly muscle, a stylohyoid muscle, a geniohyoid muscle, an infrahyoid muscle, a sternohyoid muscle, an omohyoid muscle, a sternothyroid muscle, a thyrohyoid muscle, a laryngeal muscle, a posterior cricoarytenoid muscle, a lateral cricoarytenoid muscle, an interarytenoid muscle, a cricothyroid muscle, an aryepiglottic muscle, and a thyroepiglottic muscle.

Tongue is a muscular organ in the mouth. A human tongue is known to comprise four extrinsic muscles and four intrinsic muscles. The four extrinsic muscles originate from bone and extend to the tongue, which are the genioglossus, the hyoglossus, the styloglossus and the palatoglossus. The genioglossus muscle is a tongue muscle that forms the majority of the body of the tongue. And the four intrinsic muscles of the tongue include the superior longitudinal muscle, the inferior longitudinal muscle, the vertical muscle, and the transverse muscle.

As used herein, "posterior portion of tongue" refers to a posterior part of the tongue, which is adjacent and anterior to the respiratory tract (airway). The posterior portion of tongue may include posterior portion of an extrinsic muscle or intrinsic muscle of tongue, or a combination thereof. In one embodiment, the posterior portion of tongue includes a posterior portion of genioglossus muscle.

In some embodiments, ultrasonic radio frequency data of the posterior portion of tongue is obtained by a method comprising: positioning a subject's head and neck in supine position and to the center with a Frankfort horizontal plane (FH plane), aligning an ultrasound transducer with a cross-sectional plane through the Hyoid bone and the external acoustic Meatus (HM plane) of the subject, and performing transverse cross-sectional ultrasonic scan, wherein the ultrasound transducer may be rotated (e.g., automatically by an automatic ultrasonic scanning system) with respect to the HM plane toward an anterior direction of the subject, by an angle ranging from about 0 to about 15 degrees, or rotated with respect to the HM plane toward a posterior direction of the subject, by an angle ranging from about 0 to about 15 degrees. In other words, an ultrasound scan as described above sweeping over an about 30-degree sector region would cover the posterior portion of tongue (a volume of interest).

According to certain embodiments of the present invention, an ultrasound B-mode image covering a region of interest may be first generated from radio-frequency (RF) ultrasound signals (data) and shown on a display. Then, the region of interest corresponding to tissue adjacent to airway may be selected manually or determined by a machine learning process or device. For example, a machine learning model may be trained to distinguish from a B-mode image a part of soft tissue considered as the posterior portion of tongue, and trained to distinguish from a B-mode image a part of tissue-airspace interface separating the tongue with the respiratory tract. In some embodiments, as shown in FIG. 12, the region of interest is determined as a region of a part of soft tissue 1210 subtracting a part of tissue-airspace interface 1220, wherein the part of soft tissue 1210 and the part of tissue-airspace interface 1220 are determined by one or more machine learning models.

"Machine learning model" as used herein includes at least one of: Canny edge detection, K-means clustering, nearest neighbor classification, image thresholding, two-dimensional principal component analysis, convolutional neural network, you-only-look-once (YOLO) deep learning, fully convolutional network, reinforcement-based learning, duster-based learning, hierarchical clustering, random forest, Bayesian networks, linear regression, kernel ridge regression, logistic regression, neural networks, support vector machines (SVMs), decision trees or combinations thereof.

In another aspect, the present invention provides a method for computer-aided diagnosis of obstructive sleep apnea in a subject, the method comprising:

positioning the subject with respect to an automatic ultrasonic scanning system, wherein the subject is positioned by laser alignment, aligning head and neck of the subject to a (central) sagittal plane, a Frankfort horizontal plane (FH plane), and a cross-sectional plane through the Hyoid bone and the external acoustic Meatus (HM plane) of the subject, and wherein the head and neck of the subject are positioned in supine position and positioned to the center with the FH plane perpendicular to the horizon, with an ultrasound transducer of the automatic ultrasonic scanning system aligned with the HM plane to perform a submental transverse cross-sectional ultrasonic scan, or with an ultrasound transducer of the automatic ultrasonic scanning system aligned parallel to the sagittal plane to perform a submental sagittal ultrasonic scan;

the automatic ultrasonic scanning system obtaining at least one transverse ultrasound image of upper airway of the subject, or at least one sagittal ultrasound image of upper airway of the subject;

receiving, with at least one processor, the at least one transverse ultrasound image or the at least one sagittal ultrasound image;

determining, with the at least one processor, at least one morphometric parameter based on the at least one transverse ultrasound image or the at least one sagittal ultrasound image; and determining, with the at least one processor, whether the subject is at risk of obstructive sleep apnea based on the at least one morphometric parameter, wherein a statistical value of the at least one morphometric parameter higher or lower than a threshold is indicative of the risk of obstructive sleep apnea in the subject.

In some embodiments, the sagittal plane is a central sagittal plane with respect to the subject.

Specifically, to perform the submental transverse cross-sectional ultrasonic scan, the ultrasound transducer is directed to be aligned with the HM plane and the sagittal plane, such that an imaging plane of the ultrasound transducer is aligned with the HM plane and the imaging plane of the ultrasound transducer is perpendicular to the sagittal plane; and to perform the submental sagittal ultrasonic scan, the ultrasound transducer is directed to be aligned with the HM plane and the sagittal plane, such that an imaging plane of the ultrasound transducer is parallel to the sagittal plane and the imaging plane of the ultrasound transducer is perpendicular to the HM plane.

Positioning methods for head and neck assessment known in the art (e.g., those described in US 2020/0352544 A1) can be used here.

In some embodiments, the automatic ultrasonic scanning system automatically moves the ultrasound transducer to perform a sector scan covering the HM plane, to obtain the at least one transverse ultrasound image, which is a sequence of transverse ultrasound images.

According to the present invention, the sector scan preferably covers about 0 to about 15 degrees below the HM plane and about 0 to about 15 degrees above the HM plane.

Referring to FIGS. 14A and 14B, the at least one morphometric parameter may be determined or measured using a software with or without the aid of a trained machine learning model, based on the at least one transverse ultrasound image or the at least one sagittal ultrasound image.

Embodiments consistent with the invention provide for automated prediction of the risk of OSA or diagnosis of OSA based on at least one quantitative ultrasound parameter computed from RF ultrasound data or at least one morphometric parameter of a subject. In such embodiments, a device, computer or system may be used to automatically determine the region of interest, determine the at least one quantitative ultrasound parameter and/or the at least one morphometric parameter, and/or automatically determine whether the subject is at risk of OSA.

After the region of interest is selected/determined, RF ultrasound data corresponding to the region of interest may be retrieved accordingly from the RF ultrasound data obtained from the upper airway ultrasound scan. Subsequently, the computer or computing device receives the RF ultrasound data corresponding to the region of interest, and determines at least one quantitative ultrasound parameter within the region of interest based on the RF ultrasound data. In addition, the results of quantitative ultrasound analysis may be shown as a color map on a display.

In some embodiments, a method for predicting the risk of OSA of the present invention may further comprise before the receiving step: determining a region of interest corresponding to a tissue adjacent to airway in an ultrasound image generated from RF ultrasound data of an upper airway ultrasound scan using a trained machine learning model, and/or retrieving RF ultrasound data of the tissue adjacent to airway from the RF ultrasound data of the upper airway ultrasound scan based on the region of interest determined by the trained machine learning model. The ultrasound image generated from RF ultrasound data includes but is not limited to a B-mode image.

One or more steps of a process or method disclosed herein may be implemented in an automated fashion, utilizing a computer or other electronic device to implement such steps. Such computer typically comprises a central processing unit including at least one microprocessor coupled to a memory, which may represent the random access memory (RAM) devices comprising the main storage of computer, as well as any supplemental levels of memory, e.g., cache memories, non-volatile or backup memories (e.g., programmable or flash memories), read-only memories, etc. In addition, memory may be considered to include memory storage physically located elsewhere in the computer, e.g., any cache memory in a processor in CPU, as well as any storage capacity used as a virtual memory, e.g., as stored on a mass storage device or on another computer coupled to the present computer. The computer also typically receives a number of inputs and outputs for communicating information externally. For interface with a user or operator, the computer typically comprises a user interface incorporating one or more user input devices (e.g., a keyboard, a mouse, a trackball, a joystick, a touch pad, and/or a microphone, among others) and a display (e.g., a CRT monitor, an LCD display panel, and/or a speaker). Otherwise, user input may be received via another computer or terminal.

The computer operates under the control of an operating system and executes or otherwise relies upon various computer software applications, components, programs, objects, modules, data structures, etc. Moreover, various applications, components, programs, objects, modules, etc. may also execute on one or more processors in another computer coupled to the present computer via a network, e.g., in a distributed or client-server computing environment, whereby the processing required to implement the functions of a computer program may be allocated to multiple computers over a network. As an example, the computer may include a computer aided diagnostic (CAD) system program used to implement one or more of the steps of a process or method disclosed herein. For the purposes of implementing such steps, an image database, storing medical image scans or medical scan data, may be implemented in the computer. It will be appreciated, however, that some steps in a process or method disclosed herein may be performed manually and with or without the use of computer.

As used herein, the term "quantitative ultrasound parameter" refers to parameters extracted by using quantitative ultrasound techniques, including spectral analysis and envelope statistics (Han et al., *Radiology*. 2020; 295(1):106-113; and Al-Kadi, O et al., *Ultrasound in Medicine and Biology*. 2016; 42(7):1612-26).

According to the present invention, a quantitative ultrasound parameter selected from the group consisting of an attenuation coefficient, a backscatter coefficient, and an envelope statistics parameter can be used to characterize the tissue adjacent to airway.

The term "attenuation coefficient" as used herein refers to an attenuation coefficient, or a parameter derived from or related to an attenuation coefficient, for example, a controlled attenuation parameter (M. Sasso et al., *Clinics and Research in Hepatology and Gastroenterology*. 2012; 36:13-20).

The term "backscatter coefficient" as used herein refers to a backscatter coefficient, or a parameter derived from or related to a backscatter coefficient, for example, Lizzi-Feleppa slope, intercept and midband (Han et al., *Radiology*. 2020; 295(1):106-113).

As used herein, the term "envelope statistics parameter" refers to a parameter obtained through parametric analysis by modeling the envelope-detected radio frequency signal with a statistical distribution (Han et al., *Radiology*. 2020; 295(1):106-113; and Al-Kadi, O et al., *Ultrasound in Medicine and Biology*. 2016; 42(7):1612-26); through uncertainty analysis (Tsui et al., *Scientific Reports*. 2017;7(1):41004); or through nonparametric analysis (U.S. Pat. No. 10,105,123). The statistical distribution includes but is not limited to a Rayleigh distribution, a Rician or Rice distribution, a K-distribution, a Nakagami distribution, a Nakagami-generalized inverse of Gaussian distribution, or a Homodyned-K distribution. Fitting different statistical distributions to the envelope data may yield different parametric envelope statistics, for example, a k parameter (Homodyned-K distribution), a µ parameter (Homodyned-K distribution), or an m parameter or Nakagami parameter (Nakagami distribution). Uncertainty analysis quantifies the amount of uncertainty in the value of a random variable or the outcome of a random process by parameters, including but not limited to the entropy, Shannon index, or diversity indices defined in information theory. Nonparametric analysis characterizes the data distribution by nonparametric statistics including but not limited to mean, standard deviation, median, percentiles or combinations thereof.

As used herein, the term "morphometric parameter" refers to a parameter determined based on morphological or structural sizes or dimensions (e.g., airspace width, anteroposterior location (depth) of airspace, tongue width, deep tissue thickness, superficial tissue thickness, etc.) estimated from at least one ultrasound image (e.g., an ultrasound B-mode image). In some embodiments, the morphometric parameter includes an airspace-tongue dimension ratio, for example, an airspace-tongue width ratio or an airspace-tongue thickness ratio. In some embodiments, the morphometric parameter involves a comparison of morphological dimensions of different imaging regions. For example, the morphometric parameter may be a region-to-region superficial tissue thickness ratio.

The present invention contemplates using a combination of two or more kinds of quantitative ultrasound parameters to determine the risk of OSA in a subject. For example, the risk of OSA can be determined based on a first statistical value and a second statistical value, wherein the first statistical value is a statistical value of at least one first quantitative ultrasound parameter (e.g., Nakagami parameter) in the region of interest, and the second statistical value is a statistical value of at least one second quantitative ultrasound parameter (e.g., Lizzi-Feleppa slope) in the region of interest. In some embodiments, the first and second statistical values may be given different weights.

The present invention also contemplates using a combination of at least one quantitative ultrasound parameter and at least one morphometric parameter to determine the risk of OSA in a subject.

As used herein, a higher value or lower value can refer to a value that is higher or lower compared with a reference level. For example, a lower value can be lower than a reference level by more than 1%, 5%, 10%, 15% or 20%;

and higher value can be higher than a reference level by more than 1%, 5%, 10%, 15% or 20%. In some embodiments, a reference level can be a standard (or a threshold) value in a normal individual or a control group. For example, a standard or threshold value can be set based on an average or median level obtained from a cohort of normal subjects. In some embodiments, the cohort of subjects can be a population of normal human (without OSA). In addition, a threshold value can be set further based a desired sensitivity and/or specificity for detecting or diagnosing OSA.

The risk of OSA in the subject is determined based on the at least one quantitative ultrasound parameter and/or at least one morphometric parameter, wherein a statistical value of the at least one quantitative ultrasound parameter higher or lower than a first threshold and/or a statistical value of at least one morphometric parameter higher or lower than a second threshold is indicative of the risk of OSA in the subject.

The statistical value includes but is not limited to an original value (in the case that, for example, the risk is determined based on one quantitative ultrasound parameter or morphometric parameter), a median value, a mean value, and a statistical percentile value (e.g., a $60^{th}$ percentile parameter value of a plurality of parameter values).

In some embodiments, the statistical value is a median value or a mean value of a plurality of quantitative ultrasound parameters within the region of interest.

In some other embodiments, the statistical value is a median value or a mean value of a plurality of morphometric parameter values estimated from a respective plurality of ultrasound images.

The threshold can be determined based on corresponding at least one quantitative ultrasound parameters or at least one morphometric parameters of one or more normal individuals.

According to certain embodiments of the present invention, the threshold is determined using a machine learning model as described above, trained with data (e.g., statistical values) of corresponding at least one quantitative ultrasound parameter and/or at least one morphometric parameter of one or more normal individuals and data of corresponding at least one quantitative ultrasound parameter and/or at least one morphometric parameter of one or more patients confirmed as having OSA.

Correspondingly, the present invention provides in another aspect a non-transitory computer-readable storage medium including instructions which, when executed, cause at least one processor to at least: receive or retrieve ultrasonic radio frequency data of a region of interest in upper airway of a subject; determine at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and determine whether the subject is at risk of obstructive sleep apnea based on the at least one quantitative ultrasound parameter, wherein a statistical value of the at least one quantitative ultrasound parameter higher or lower than a threshold is indicative of the risk of obstructive sleep apnea in the subject.

Also provided is a non-transitory computer-readable storage medium including instructions which, when executed, cause at least one processor to at least: receive at least one transverse ultrasound image or at least one sagittal ultrasound image of upper airway of a subject; determine at least one morphometric parameter based on the at least one transverse ultrasound image or the at least one sagittal ultrasound image; and determine whether the subject is at risk of obstructive sleep apnea based on the at least one morphometric parameter, wherein a statistical value of the at least one morphometric parameter higher or lower than a threshold is indicative of the risk of obstructive sleep apnea in the subject.

In a further aspect, the present invention provides a method for computer-aided diagnosis of obstructive sleep apnea (OSA) in a subject, the method comprising:

positioning the subject with respect to an automatic ultrasonic scanning system;

scanning, with the automatic ultrasonic scanning system, a location corresponding to upper airway of the subject, to obtain ultrasonic radio frequency data;

receiving or retrieving, with at least one processor, ultrasonic radio frequency data of a region of interest in upper airway of a subject, wherein the region of interest corresponds to a tissue adjacent to airway of the subject;

determining, with the at least one processor, at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and determining, with the at least one processor, whether the subject is at risk of obstructive sleep apnea based on the at least one quantitative ultrasound parameter, wherein a statistical value of the at least one quantitative ultrasound parameter higher or lower than a threshold is indicative of the risk of obstructive sleep apnea in the subject.

Preferably, the subject is positioned by laser alignment. With laser beam guidance, the subject's head and neck is aligned to a sagittal plane, a Frankfort horizontal plane (FH plane), and a cross-sectional plane through the Hyoid bone and the external acoustic Meatus (HM plane) of the subject. More specifically, the head and neck of the subject are positioned in supine position and then positioned to the center with the FH plane perpendicular to the horizon, with an ultrasound transducer of the automatic ultrasonic scanning system aligned with the HM plane to perform transverse cross-sectional ultrasonic scan.

In some embodiments, the automatic ultrasonic scanning system is incorporated with one or more laser projectors for positioning head and neck, such as automatic ultrasonic scanning system 100 as shown in FIG. 1. Laser projector 120a projects a laser beam b1 for guiding the head positioning with respect to a central sagittal plane. Laser projector 120b projects a laser beam b2 for guiding the head positioning with respect to an FH plane, and a laser beam b3 for guiding the positioning of ultrasound transducer 110 with respect to an HM plane. After the positioning is completed, transducer holder 130 of automatic ultrasonic scanning system 100 rotates with respect to the HM plane, such that ultrasound transducer 110 held therein sweeps around the HM plane to perform an automatic scan.

Also provided is a system configured to perform the above-described methods for computer-aided diagnosis of obstructive sleep apnea (OSA) in a subject.

According to certain embodiments of the present invention, the system comprises an automatic ultrasonic scanning system and a computer.

The automatic ultrasonic scanning system is equipped with one or more laser projectors for positioning head and neck of the subject, and is used for scanning a location corresponding to upper airway of the subject to obtain ultrasonic radio frequency data.

The computer comprises a non-transitory storage medium and at least one processor, the non-transitory storage medium including instructions which, when executed, cause the at least one processor to at least: receive ultrasonic radio frequency data of a region of interest in upper airway of a subject from the automatic ultrasonic scanning system, wherein the region of interest corresponds to a tissue adjacent to airway of the subject; determine at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and determine whether the subject is at risk of obstructive sleep apnea based on the at least one quantitative ultrasound parameter, wherein a statistical value of the at least one quantitative ultrasound parameter higher or lower than a threshold is indicative of the risk of obstructive sleep apnea in the subject.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

Example 1. OSA Risks Prediction by Quantitative Ultrasound Parameters

The study was conducted at Stanford Sleep Medicine and Surgery clinic with approval by Stanford School of Medicine institutional review board (IRB: 53172) for subjects with a polysomnography (PSG) or a home sleep study (given the pandemic restrictions on access to PSGs). Inclusion criteria were adults over 18 years with a diagnosis of obstructive sleep apnea (OSA) obtained through in-lab or home sleep testing PSG study. All subjects have consented to participate in the study. The time difference between PSG and ultrasound scan was less than 3 years (1095 days), with body mass index (BMI) change of less than 10%. If BMI was not noted on the PSG report, then the date difference between sleep study report and ultrasound scan was less than 180 days. Exclusion criteria included subjects missing sleep study data or had PSG results greater than 3 years or if there is a 10% difference in the BMI between the time of examination and sonographic evaluation. Standard of care for OSA patients included full history, clinical exam, and nasopharyngoscopy.

We standardized the submental ultrasound scan using a laser alignment tool and applied BUI technology to the upper airway scans in our cohort. The raw data was used to generate the corresponding parametric map consisting of Nakagami parameters to correlate with the OSA severity. As proof of concept, subjects with different OSA severity levels, in particular, normal or mild with AHI<15 events/hour and moderate to severe with AHI≥15 events/hour, were compared.

1. Methods
1.1 Ultrasound Setup
An FDA-cleared ultrasound scanner, Terason™ uSmart3200T (K193510) with a convex transducer (5C2A), was used to scan and obtain the radio-frequency (RF) ultrasound signals and the ultrasound B-mode images. We analyzed the RF ultrasound signals using an FDA-cleared software device, AmCAD-US (K162574) to characterize upper airway muscle. Laser beams (FDA Registered Establishment Number 3015218501) were used to align subject position to the sagittal plane, the Frankfort horizontal plane (FH plane) and a cross-sectional plane through the Hyoid bone and the external acoustic Meatus (HM plane) as illustrated in FIG. 1. The head and neck of the subjects were positioned in supine position and then positioned to the center with the FH plane perpendicular to the horizon with the ultrasound transducer aligned with the laser projection of the HM plane to obtain transverse cross-sectional ultrasound images such as one shown in the right of FIG. 2A. The transducer performed the scan automatically to avoid operator dependency by manual scan. The automatic scan swept over a 30-degree sector region 250 of the upper airway (a volume of interest, corresponding to a posterior portion of the tongue) that could be divided into A, B, C, and D sites as shown in FIG. 2B. These sites were considered consistent with the VOTE classification used for drug-induced sleep endoscopy (DISE). The 30-degree sector region 250 covers an HM plane 260 corresponding to the laser beam-defined HM plane as mentioned above, the HM plane 260 dividing the B and C sites.

1.2 Nakagami Parameter
The ultrasound backscattered signals from a region of interest (ROI) sized 1.7 cm×1.7 at the posterior of the tongue, indicated as the region framed by the black square in FIG. 3, were extracted for statistical analysis. The analysis started with taking the absolute value of the Hilbert transformation of the RF ultrasound signals to obtain the echo amplitude (echo intensity) data, which was log-compressed to form the B-mode ultrasound image, as shown in FIG. 3, (a) and (c). By analyzing the statistical distribution of the echo intensity, different backscattered statistics to assess human tissue properties have been proposed (Ho et al., *PLoS One*. 2013;8(5):e63543; and Zhou et al., *Ultrasonics*. 2020; 101:106001), one of which was the Nakagami parameter. The Nakagami parameter value is a statistic of the Nakagami distribution estimated based on the echo intensity data within a window in the ROI. As shown in FIG. 4, the window 410, with size of 0.3-by-0.3 cm, starting from the corner of the ROI 400, slides laterally and then axially with an overlap rate of 95% to cover the entire ROI 400, wherein the overlap rate equals to overlapping area of two adjacent windows/area of window. The Nakagami parameter calculation was repeated for each sliding window to construct the BUI color maps as shown in FIG. 3, (b) and (d).

The Nakagami parameter value (hereinafter referred to as "BUI value") ranging from 0 to 1 indicated the changes in the shape of the echo intensity distribution from pre-Rayleigh distribution with a longer right tail (BUI value<1) to a Rayleigh distribution (BUI value=1). BUI value higher than 1 showed a post-Rayleigh distribution shape with a shorter right tail. This study focused on analysis of the BUI values at different locations along the upper airway. Together with the BMI and age, we attempted to investigate how the muscle quality, in terms of the echoed and backscattered ultrasonic signals, was correlated to the severity of OSA besides the obesity and age factors.

1.3 Statistical Analysis
The median BUI value and median echo intensity from the ROI were used for statistical analysis. Statistical comparisons of different OSA severity levels and the power of differentiating the moderate-to-severe OSA were tested using nonparametric Mann-Whitney tests. Stratified analyses were performed for different BMI and age subgroups. Logistic regression models were then built using the significant factors to estimate the risk of moderate-to-severe OSA. Statistical significance was set at p<0.05.

2. Results

Eighty-nine (89) patients met the inclusion criteria with 70 males and 19 females. Mean age was 38.8±12.7, mean BMI of 26.7±5.0, and mean AHI of 17.5±16.8. Subjects meeting inclusion criteria were consented at the Stanford Sleep Surgery Clinic between July 2020 and March 2022 (see Table 1 below).

ent with p-value<0.05. For the echo intensity (FIG. 5), only the group of severe OSA (AHI≥30) was found significantly different from other groups. For the BUI value (FIG. 6), a clear increasing trend of the BUI value could be observed from the normal to the severe group for both the B and the A regions. Two pairs of echo intensity and BUI color maps computed from mild and moderate OSA patients, respectively, are shown in FIG. 3. Difference in the visual representation of the BUI values is more prominent than that of the B-mode image (echo intensity map).

TABLE 1

Demographic data of subjects recruited to the study

| | Overall | No OSA (AHI < 5) | Mild OSA (5 ≤ AHI < 15) | Moderate OSA (15 ≤ AHI < 30) | Severe OSA (30 ≤ AHI) | P-Value |
|---|---|---|---|---|---|---|
| Sample Size [n] | 89 | 18 | 35 | 20 | 16 | — |
| Age [years] | 38.8 ± 12.7 | 34.4 ± 13.3 | 35.7 ± 10.8 | 43.5 ± 12.4 | 44.6 ± 13.5 | 0.0010 |
| BMI [kg/m$^2$] | 26.7 ± 5 | 25.3 ± 5.2 | 25.1 ± 3.8 | 27.6 ± 4.4 | 30.7 ± 5.7 | 0.0002 |
| Male [n] (%) | 70 (78.7) | 12 (66.7) | 28 (80) | 18 (90) | 12 (75) | 0.438 |
| Race [n] (%) | | | | | | — |
| White | 46 (51.7) | 10 (55.6) | 16 (45.7) | 12 (60) | 8 (50) | |
| Black/African American | 2 (2.2) | 0 (0) | 2 (5.7) | 0 (0) | 0 (0) | |
| Asian | 22 (24.7) | 6 (33.3) | 10 (28.6) | 4 (20) | 2 (12.5) | |
| Other | 19 (21.3) | 2 (11.1) | 7 (20) | 4 (20) | 6 (37.5) | |
| AHI [e/hr] | 17.5 ± 16.8 | 2.0 ± 1.4 | 9.0 ± 2.9 | 21.8 ± 4.0 | 48.0 ± 12.2 | <0.0001 |
| Study type [n] (%) | | | | | | — |
| PSG | 64 (71.9) | 11 (61.1) | 23 (65.7) | 18 (90) | 12 (75) | |
| HST | 25 (28.1) | 7 (38.9) | 12 (34.3) | 2 (10) | 4 (25) | |
| Echo Intensity, D region | 230.20 ± 91.94 | 244.33 ± 106.35 | 226.79 ± 79.38 | 230.10 ± 105.21 | 221.89 ± 90.13 | 0.7827 |
| Echo Intensity, C region | 260.12 ± 80.32 | 263.90 ± 78.49 | 264.46 ± 66.82 | 244.70 ± 77.78 | 265.65 ± 112.57 | 0.4223 |
| Echo Intensity, B region | 232.35 ± 74.82 | 209.86 ± 38.81 | 230.84 ± 62.94 | 213.50 ± 63.88 | 284.50 ± 114.02 | 0.3938 |
| Echo Intensity, A region | 184.70 ± 61.04 | 171.38 ± 49.04 | 177.82 ± 57.57 | 174.87 ± 33.85 | 227.03 ± 88.35 | 0.0945 |
| BUI value, D region | 0.797 ± 0.066 | 0.785 ± 0.054 | 0.794 ± 0.067 | 0.812 ± 0.069 | 0.801 ± 0.074 | 0.2099 |
| BUI value, C region | 0.807 ± 0.058 | 0.779 ± 0.058 | 0.810 ± 0.051 | 0.815 ± 0.060 | 0.822 ± 0.062 | 0.0836 |
| BUI value, B region | 0.816 ± 0.066 | 0.767 ± 0.060 | 0.812 ± 0.066 | 0.848 ± 0.057 | 0.840 ± 0.054 | 0.0007 |
| BUI value, A region | 0.806 ± 0.097 | 0.776 ± 0.082 | 0.773 ± 0.104 | 0.828 ± 0.086 | 0.887 ± 0.043 | <0.0001 |

Data are mean ± SD unless otherwise indicated
P-value: AHI < 15 vs. AHI ≥ 15
Mann-Whitney Test for continuous data
Fisher's Exact Test for categorical data Fifty-three (53) subjects had an AHI below 15 events/hour. As a proof of concept, the BUI technology was applied to the upper airway in a cohort of OSA patients and its effects were tested. Different levels of the upper airway were assessed based on the sector areas covered by the transducer rotation movement, including A, B, C, and D regions as seen in FIG. 2B. Also shown in Table 1 were the statistics (mean and standard deviation) of the ultrasound measurements, including the echo intensity and the BUI value, of subjects grouped according to the OSA severity levels. As some ultrasonic data were not normally distributed, the Mann-Whitney Test was used to test the statistical significance between the group with AHI<15 and the group with AHI≥15. As can be seen, the significant differences of ultrasound measurements could be found at the A and B regions. FIGS. 5-6 show in further detail the box plots of the echo intensity and BUI values for the four groups of OSA severity and those pairs compared to be significantly differ- The upper half of the sector area scanned was further divided into four sub-regions, denoted as A1, A2, B1, and B2 in FIG. 2C, and the BUI measurements from all four sub-regions have shown significant differentiation power for moderate-to-severe OSA from no or mild OSA (p<0.0001, p=0.0002, p=0.0002, and p=0.0157), as shown in FIG. 7. Higher BUI values at B1, A2 and A1 are associated with more severe AHI, even after controlling for covariates (BMI and age), with partial correlation coefficient of 0.32, 0.32, and 0.30, respectively (FIG. 8). The echo intensities from 4 sub-regions have not shown significant differentiation power for moderate-to-severe OSA from no or mild OSA.

BUI measurements were stratified for the confounding variables, where BMI of 25 kg/m$^2$ and age of 40 were used as cutoff. 57% of subjects with AHI<15 and 28% of subjects with AHI≥15 have normal BMI (BMI≤25 kg/m 2). 74% of subjects with AHI<15 and 39% of subjects with AHI≥15 are below age of 40. As shown in FIG. 9, BUI values were higher at A1 and A2 sub-regions in the BMI≥25 and AHI≥15 cohort (p=0.0017 and p=0.0050, respectively). Whereas for BMI<25 cohort, BUI value from B1 sub-region (p=0.0060) was most significant for differentiating moderate-to-severe OSA from no or mild OSA. The power of differentiating for moderate-to-severe OSA using BUI measurements increased when the analysis region steered from the B2 to the A1 for Age<40 cohort (FIG. 10), while significant differences are found in the BUI value from A1 and B1 for Age≥40 cohort (p=0.0195 and p=0.0002).

In the normal BMI group, BUI value from B1 and A1 independently estimates moderate-to-severe OSA risk with an area under the receiver operating characteristic (AUROC) of 0.83 (95% confidence interval (95% CI): 0.678 to 0.930). BMI, age, and BUI value from A2 combined estimate moderate-to-severe OSA risk in the overweight-obese group with an AUROC of 0.873 (95% CI: 0.747 to 0.951) (FIG. 11).

Referring to FIG. 13 illustrating an exemplary determination of threshold for high/moderate/low risk of moderate-to-severe OSA (AHI≥15), an intercept point where Sensitivity=0.58 and Specificity=0.96 in the AUROC curve (the same as that of FIG. 11, (b)) is chosen and corresponds to a BUI value threshold of 0.78 for "high risk" of OSA, and an intercept point where Sensitivity=0.92 and Specificity=0.70 in the AUROC curve is chosen and corresponds to a BUI value threshold of 0.39 for "moderate risk" of OSA.

Example 2. OSA Risks Prediction by Airway/Airway Tissue Configurations

This prospective study was approved by the institutional review board (IRB: 53172) to conduct at Stanford University Sleep Surgery Clinic. Patients≥18 years with an attended or unattended polysomnography (PSG) and limited body mass index (BMI) change (<10%) within 3 years were recruited to participate in the study. We standardized the submental ultrasound scan using a laser alignment tool to observe the upper airway of the subject in supine position during tidal respiration. Features of the upper airway anatomy were extracted and quantified from 49 normal (BMI<25) and 81 overweight (BMI≥25) subjects to compare with their OSA severity.

1. Methods 1.1 Ultrasound Scan Setup

Terason™ uSmart 3200T (K193510) with a 5C2A convex transducer (K150533) was used to scan and obtain the B-mode images of the upper airway. Laser beams (FDA Registered Establishment Number 3015218501) were used to position the subject's Frankfort horizontal plane (FH plane) upright and to aim the transducer through the Hyoid bone and the external acoustic Meatus (HM plane) (see FIG. 1). A 30-degree sector scan, which covers 15 degrees below and above the HM plane, was performed automatically aided with the laser alignment tool avoiding possible bias in manual scanning to acquire a sequence of transverse B-mode images of the upper airway.

1.2 Analysis of Upper Airway Tissue and Airway Morphology

The transverse width, depth and thickness of the upper airway and tissue during tidal respiration were measured on the B-mode images (see, e.g., FIG. 14A) acquired from the ultrasound submental sector scan. The 30-degree sector scan was divided into 4 equiangular regions A, B, C, and D (FIG. 2B), and the superficial and deep tissues imaged in each region were described in Table 2 below. The superficial tissues were mainly subcutaneous fat and suprahyoid muscles while the deep tissue mainly consisted of the soft palate, tongue, or epiglottis, depending on the region imaged.

TABLE 2

Tissues imaged by the ultrasound scan in each of the 4 regions

| Region | Superficial Tissue | Deep Tissue |
| --- | --- | --- |
| A (Velum) | Subcutaneous Fat + Suprahyoid Muscles | Tongue + Velum |
| B (Oropharyngeal) | Subcutaneous Fat + Suprahyoid Muscles | Tongue + (maybe some) Velum |
| C (Tongue Base) | Subcutaneous Fat + Suprahyoid Muscles | Tongue |
| D (Epiglottis) | Subcutaneous Fat + Suprahyoid Muscles | Epiglottis |

1.3 Statistical Analysis

AmCAD-UO analysis software (K180867) was used to measure the maximum width and depth of the upper airway, the maximum thickness of the superficial and deep tissues, and the maximum tongue width at each of the 4 regions. Relative measurements such as the airspace to tongue width ratio, region-to-region superficial tissue thickness ratio and region-to-region deep tissue thickness ratio were calculated to characterize the anatomic morphology. All the direct and relative measurements of airway and tissue dimensions were included, and median of the measurements obtained from three repetitive scans were extracted for statistical analysis. The differences between the moderate-to-severe OSA group and the no-to-mild OSA group stratified by the BMI (normal with BMI<25 and obese with BMI>25) were analyzed using nonparametric Mann-Whitney tests. Statistical significance was set at p-valueless than 0.05.

2. Results

A hundred and thirty patients (28 females) were included between July 2020 and October 2022 with mean age 41.3 years, mean BMI 27.1 kg/m 2, and mean AHI 20.2 events/hour (see Table 3 below). 46% of the patients had an AHI≥15 events/h and 59% of the patients were Caucasian. While both age and BMI were significantly higher in patients with AHI≥15 (p<0.0001), there were no significant differences in BMI and AHI between Caucasians and non-Caucasians. However, non-Caucasians included were younger than Caucasians (p=0.0346).

TABLE 3

Demographic of subjects recruited for the study

|  | Overall | No OSA (AHI < 5) | Mild OSA (5 ≤ AHI < 15) | Moderate OSA (15 ≤ AHI < 30) | Severe OSA (30 ≤ AHI) | P-Value (AHI, 15) |
| --- | --- | --- | --- | --- | --- | --- |
| Sample Size [n] | 130 | 24 | 46 | 33 | 27 |  |
| Age [years] | 41.3 ± 12.8 | 37.8 ± 12.4 | 36.0 ± 9.9 | 45.4 ± 13.1 | 48.6 ± 12.6 | P < 0.0001 |

TABLE 3-continued

Demographic of subjects recruited for the study

|  | Overall | No OSA (AHI < 5) | Mild OSA (5 ≤ AHI < 15) | Moderate OSA (15 ≤ AHI < 30) | Severe OSA (30 ≤ AHI) | P-Value (AHI, 15) |
|---|---|---|---|---|---|---|
| BMI [kg/m2] | 27.1 ± 4.6 | 25.3 ± 3.8 | 25.3 ± 4.1 | 27.6 ± 4.3 | 31.1 ± 4.0 | P < 0.0001 |
| Male/Female [n] | 102/28 | 16/8 | 37/9 | 28/5 | 21/6 | N.S. |
| Race [n] | | | | | | |
| Caucasian | 77 | 14 | 25 | 23 | 15 | |
| Black/African American | 2 | 0 | 2 | 0 | 0 | |
| Asian | 26 | 6 | 11 | 5 | 4 | |
| Other | 25 | 4 | 8 | 5 | 8 | |
| AHI [events/h] | 20.2 ± 20.2 | 1.9 ± 1.4 | 9.0 ± 2.9 | 21.6 ± 4.0 | 53.8 ± 16.9 | P < 0.0001 |

The statistics and comparison of the airspace and tissue dimensions for the studied population, normal BMI group and obese groups were summarized in Table 4 below. The obese group with AHI≥15 had significantly narrower airspace at regions A, B and C with p values ranging from 0.0022 to 0.0357 and the antero-posterior location of the airspace at regions A and B are significantly deeper with p=0.0072 and 0.0195, respectively. For the normal BMI group, only the airspace width showed a significant difference (p=0.0183). FIG. 15 shows the comparisons of the width and antero-posterior location of the airspace for region A. While the tongue width and the deep tissue thickness were not different at all regions for the normal BMI group, the obese group with AHI≥15 were observed with significantly wider (p=0.00080.0096) tongue and thicker (p=0.0043~0.0353) deep tissue. FIG. 16 shows the comparison of the tongue width at region C and the comparison of the deep tissue thickness at region A.

TABLE 5

The morphometric relative measurements, in mean ± SD, of the tissue and airway in normal, overweight and all subjects

| Morphometrics | Region | AHI < 15 (n = 70) | AHI ≥ 15 (n = 60) | P-Value |
|---|---|---|---|---|
| Airspace-Tongue Width Ratio | A | 0.86 ± 0.16 | 0.60 ± 0.33 | P < 0.0001 |
| | B | 0.88 ± 0.20 | 0.69 ± 0.29 | P < 0.0001 |
| | C | 0.90 ± 0.21 | 0.72 ± 0.26 | P < 0.0001 |
| | D | 0.87 ± 0.20 | 0.75 ± 0.22 | P = 0.0007 |
| Region-to-Region Deep Tissue Thickness Ratio | A/B | 1.05 ± 0.05 | 1.06 ± 0.05 | P = 0.1749 |
| | A/C | 1.20 ± 0.09 | 1.22 ± 0.11 | P = 0.2264 |
| | A/D | 1.41 ± 0.23 | 1.43 ± 0.22 | P = 0.7349 |
| Region-to-Region Superficial Tissue Thickness Ratio | A/B | 1.04 ± 0.06 | 1.02 ± 0.04 | P = 0.0271 |
| | A/C | 1.07 ± 0.09 | 1.02 ± 0.07 | P = 0.0036 |
| | A/D | 1.04 ± 0.12 | 1.00 ± 0.10 | P = 0.0454 |

The p-values are results of Mann-Whitney tests between no-to-mild OSA subgroup and moderate-to-severe OSA subgroup

TABLE 4

The dimensions, in mean ± SD, of the tissue and airway in normal, overweight and all subjects.

| Morphometrics | Region | BMI < 25 | | | BMI ≥ 25 | | | All Subjects | | |
|---|---|---|---|---|---|---|---|---|---|---|
| | | AHI < 15 (n = 37) | AHI ≥ 15 (n = 12) | P-Value | AHI < 15 (n = 33) | AHI ≥ 15 (n = 48) | P-Value | AHI < 15 (n = 70) | AHI ≥ 15 (n = 60) | P-Value |
| Airspace Width | A | 4.20 ± 0.91 | 3.03 ± 1.91 | P = 0.0183 | 4.19 ± 0.56 | 3.16 ± 1.63 | P = 0.0022 | 4.20 ± 0.76 | 3.14 ± 1.67 | P < 0.0001 |
| | B | 4.12 ± 0.80 | 3.68 ± 1.36 | P = 0.2498 | 3.97 ± 0.82 | 3.36 ± 1.40 | P = 0.0123 | 4.05 ± 0.81 | 3.42 ± 1.39 | P = 0.0009 |
| | C | 3.78 ± 0.74 | 3.11 ± 1.65 | P = 0.3896 | 3.75 ± 0.85 | 3.41 ± 1.00 | P = 0.0357 | 3.77 ± 0.79 | 3.35 ± 1.15 | P = 0.0117 |
| | D | 3.47 ± 0.53 | 3.39 ± 0.73 | P = 0.7802 | 3.32 ± 0.79 | 3.10 ± 0.88 | P = 0.1414 | 3.40 ± 0.67 | 3.16 ± 0.86 | P = 0.0319 |
| Airspace Depth | A | 5.58 ± 0.73 | 5.59 ± 0.80 | P = 0.7625 | 5.66 ± 0.72 | 5.94 ± 0.77 | P = 0.0072 | 5.62 ± 0.72 | 5.87 ± 0.78 | P = 0.0082 |
| | B | 5.11 ± 0.73 | 4.83 ± 0.95 | P = 0.3896 | 5.21 ± 0.70 | 5.44 ± 0.76 | P = 0.0195 | 5.16 ± 0.71 | 5.32 ± 0.83 | P = 0.0444 |
| | C | 4.57 ± 0.67 | 4.38 ± 0.94 | P = 0.5768 | 4.77 ± 0.68 | 5.00 ± 0.63 | P = 0.0827 | 4.66 ± 0.68 | 4.88 ± 0.73 | P = 0.0631 |
| | D | 4.21 ± 0.59 | 4.26 ± 0.48 | P = 0.5689 | 4.41 ± 0.59 | 4.71 ± 0.54 | P = 0.0650 | 4.30 ± 0.60 | 4.62 ± 0.55 | P = 0.0392 |
| Tongue Width | A | 4.73 ± 0.49 | 4.96 ± 0.59 | P = 0.1630 | 4.96 ± 0.58 | 5.33 ± 0.59 | P = 0.0096 | 4.84 ± 0.54 | 5.25 ± 0.61 | P = 0.0001 |
| | B | 4.53 ± 0.54 | 4.69 ± 0.66 | P = 0.2954 | 4.75 ± 0.53 | 5.17 ± 0.62 | P = 0.0019 | 4.63 ± 0.54 | 5.07 ± 0.65 | P = 0.0001 |
| | C | 4.20 ± 0.50 | 4.26 ± 0.60 | P = 0.6009 | 4.37 ± 0.52 | 4.86 ± 0.64 | P = 0.0008 | 4.28 ± 0.51 | 4.74 ± 0.67 | P < 0.0001 |
| | D | 3.91 ± 0.48 | 3.84 ± 0.64 | P = 0.9444 | 3.97 ± 0.55 | 4.46 ± 0.64 | P = 0.0012 | 3.94 ± 0.51 | 4.33 ± 0.68 | P = 0.0003 |
| Deep Tissue Thickness | A | 4.69 ± 0.55 | 4.67 ± 0.54 | P = 0.8161 | 4.75 ± 0.49 | 5.09 ± 0.58 | P = 0.0043 | 4.72 ± 0.52 | 5.01 ± 0.59 | P = 0.0044 |
| | B | 4.50 ± 0.58 | 4.30 ± 0.50 | P = 0.3288 | 4.52 ± 0.52 | 4.84 ± 0.54 | P = 0.0064 | 4.51 ± 0.55 | 4.73 ± 0.57 | P = 0.0259 |
| | C | 3.94 ± 0.59 | 3.80 ± 0.56 | P = 0.4292 | 3.95 ± 0.63 | 4.22 ± 0.64 | P = 0.0353 | 3.94 ± 0.60 | 4.13 ± 0.64 | P = 0.0832 |
| | D | 3.40 ± 0.53 | 3.16 ± 0.58 | P = 0.2135 | 3.40 ± 0.61 | 3.69 ± 0.59 | P = 0.0281 | 3.40 ± 0.56 | 3.58 ± 0.62 | P = 0.0752 |

The p-value are results of Mann-Whitney tests between no-to-mild OSA subgroup and moderate-to-severe OSA subgroup.

Table 5 below summarizes the statistical comparisons of the morphometric relative measurements. The airspace-tissue width ratio, that compares the airspace size to the tongue size, was smaller in patients with AHI≥15, most prominently seen at region A (p<0.0001 and p=0.0334 for overweight-obese and normal BMI group, respectively, as shown in FIG. 17, (a)).

For the obese group with AHI≥15, this ratio was also significantly smaller at regions B, C and D (p=0.0003~0.0072). For the region-to-region deep tissue thickness ratio that characterized the tongue shape, only the normal BMI patients with AHI≥15 were observed to have thicker deep tissue at region A compared to region B (p=0.0408), shown in FIG. 17, (b). The region-to-region superficial tissue thickness ratio was intended to describe the chin anatomy. Again, only the normal BMI patients with AHI≥15 were observed to have a thicker superficial tissue at region D compared to region A (p=0.0201), shown in FIG. 17, (c).

With the significant anatomic factors found to be significantly different in patients with the moderate-to-severe OSA, predictive models were constructed to estimate the risk of moderate-to-severe OSA. For the normal BMI group, the airspace width at region A and the superficial tissue thickness ratio between regions A and D were selected into the model with the AUROC reaching 0.82 (95% CI: 0.684 to 0.915, FIG. 18, (a)). The risk predictive model with age and the airspace-tissue width ratio at region A included in the model for the obese group had an AUROC of 0.835 (95% CI: 0.736 to 0.908, FIG. 18, (b)).

Example 3. Screening of OSA Patients Responsive to Mandibular Advancement Device (MAD) Treatment by Airway/Airway Tissue Configurations Mandibular advancement device (MAD) is designed to pull the mandible and the tongue forward anteriorly to increase the cross-sectional airway dimension and thus possibly reduce airway obstructions during sleep. The effectiveness of a MAD may be affected by the pre-treatment OSA severity, BMI, and degree of changes in pharyngeal dimensions resulting from the device in situ. In this study, 3D submental ultrasound imaging is applied to evaluate the difference in the tongue and airway configurations between the responders and non-responders of the MAD treatment.
1. Methods In this retrospective study, 31 subjects (25 males, median age/BMI/baseline AHI of 56/24.5/25.3) diagnosed with sleep apnea and underwent tongue-backing-MAD (t-MAD) treatment were consented from the Department of dentistry of National Taiwan University Hospital between April and December 2022 (IRB 202108078RIPD). Changes in the severity of OSA were assessed with polysomnographic studies. Success of t-MAD treatment was defined by an AHI of less than 10 events/hour and at least 50% decrease in AHI from baseline. There were no significant differences in age, BMI, gender and baseline AHI between responders (n=17) and non-responders (n=14). While awake and lying in supine position, the tongue and airway configurations at retropalatal and retroglossal regions without and with t-MAD in situ were assessed with a standardized 3D submental ultrasound imaging system AmCAD-UO (AmCAD BioMed Corp., Taiwan). Statistical comparisons were performed using t-tests, chi-square tests and nonparametric Mann-Whitney tests.
2. Results The anteroposterior location of the tongue-airway interface at retroglossal region, relative to the superior-inferior location of the soft-palate-airway interface, was found significantly reduced in responders when t-MAD is in situ (p=0.0124). The cross-sectional area of the deep tissue at soft-palate region relative to retroglossal region was found to be significantly smaller in responders (p=0.0070). 13 responders (76.5%) and 9 non-responders (64.3%) were observed with airway width increase in the retroglossal region with t-MAD in situ. However, the difference in airway width changes between responders and non-responders was not statistically significant possibly due to the limited sample size.

What is claimed is:

1. A computer-implemented method for predicting the risk of obstructive sleep apnea in a subject, comprising:
receiving, with at least one processor of the computer, ultrasonic radio-frequency data of a region of interest in upper airway of the subject, wherein the region of interest corresponds to a tissue adjacent to airway of the subject;
determining, with the at least one processor of the computer, at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and
determining, with the at least one processor of the computer, whether the subject is at risk of obstructive sleep apnea based on the at least one quantitative ultrasound parameter, wherein a statistical value of the at least one quantitative ultrasound parameter higher or lower than a threshold is indicative of the risk of obstructive sleep apnea in the subject.

2. The method of claim 1, wherein the region of interest includes a posterior portion of tongue of the subject.

3. The method of claim 1, wherein the threshold is determined based on corresponding at least one quantitative ultrasound parameter of one or more normal individuals.

4. The method of claim 3, wherein the threshold is determined using a machine learning model trained with data of the corresponding at least one quantitative ultrasound parameter of one or more normal individuals and data of corresponding at least one quantitative ultrasound parameter of one or more patients confirmed as having obstructive sleep apnea.

5. A method for computer-aided diagnosis of obstructive sleep apnea in a subject, the method comprising:
positioning the subject with respect to an automatic ultrasonic scanning system;
scanning, with the automatic ultrasonic scanning system, a location corresponding to upper airway of the subject, to obtain ultrasonic radio frequency data;
receiving, with at least one processor of the computer, ultrasonic radio frequency data of a region of interest in upper airway of a subject, wherein the region of interest corresponds to a tissue adjacent to airway of the subject;
determining, with the at least one processor of the computer, at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and
determining, with the at least one processor of the computer, whether the subject is at risk of obstructive sleep apnea based on the at least one quantitative ultrasound parameter, wherein a statistical value of the at least one quantitative ultrasound parameter higher or lower than a threshold is indicative of the risk of obstructive sleep apnea in the subject.

6. The method of claim 5, wherein the subject is positioned by laser alignment, aligning head and neck of the subject to a sagittal plane, a Frankfort horizontal plane (FH plane), and a cross-sectional plane through the Hyoid bone and the external acoustic Meatus (HM plane) of the subject.

7. The method of claim 6, wherein the head and neck of the subject are positioned in supine position and positioned to the center with the FH plane perpendicular to the horizon, with an ultrasound transducer of the automatic ultrasonic scanning system aligned with the HM plane to perform transverse cross-sectional ultrasonic scan.

8. The method of claim 5, wherein the region of interest includes a posterior portion of tongue of the subject.

9. The method of claim 5, wherein the threshold is determined based on corresponding at least one quantitative ultrasound parameters of one or more normal individuals.

10. The method of claim 9, wherein the threshold is determined using a machine learning model trained with data of the corresponding at least one quantitative ultrasound parameter of one or more normal individuals and data of corresponding at least one quantitative ultrasound parameter of one or more patients confirmed as having obstructive sleep apnea.

11. A system for diagnosing obstructive sleep apnea in a subject, comprising:
- at least one processor; and
- a non-transitory computer-readable storage medium including instructions which, when executed, cause the at least one processor to:
- receive ultrasonic radio frequency data of a region of interest in upper airway of a subject, wherein the region of interest corresponds to a tissue adjacent to airway of the subject;
- determine at least one quantitative ultrasound parameter within the region of interest based on the ultrasonic radio frequency data, wherein the at least one quantitative ultrasound parameter is at least one attenuation coefficient, at least one backscatter coefficient, or at least one envelope statistics parameter; and
- determine whether the subject is at risk of obstructive sleep apnea based on the at least one quantitative ultrasound parameter, wherein a statistical value of the at least one quantitative ultrasound parameter higher or lower than a threshold is indicative of the risk of obstructive sleep apnea in the subject.

12. A method for computer-aided diagnosis of obstructive sleep apnea in a subject, the method comprising:
- positioning the subject with respect to an automatic ultrasonic scanning system, wherein the subject is positioned by laser alignment, aligning head and neck of the subject to a sagittal plane, a Frankfort horizontal plane (FH plane), and a cross-sectional plane through the Hyoid bone and the external acoustic Meatus (HM plane) of the subject, and wherein the head and neck of the subject are positioned in supine position and positioned to the center with the FH plane perpendicular to the horizon, with an ultrasound transducer of the automatic ultrasonic scanning system aligned with the HM plane to perform transverse cross-sectional ultrasonic scan, or with an ultrasound transducer of the automatic ultrasonic scanning system aligned parallel to the sagittal plane to perform sagittal ultrasonic scan;
- the automatic ultrasonic scanning system obtaining at least one transverse ultrasound image of upper airway of the subject, or at least one sagittal ultrasound image of upper airway of the subject;
- receiving, with at least one processor of the computer, the at least one transverse ultrasound image or the at least one sagittal ultrasound image;
- determining, with the at least one processor of the computer, at least one morphometric parameter based on the at least one transverse ultrasound image or the at least one sagittal ultrasound image; and
- determining, with the at least one processor of the computer, whether the subject is at risk of obstructive sleep apnea based on the at least one morphometric parameter, wherein a statistical value of the at least one morphometric parameter higher or lower than a threshold is indicative of the risk of obstructive sleep apnea in the subject.

13. The method of claim 12, wherein the automatic ultrasonic scanning system automatically moves the ultrasound transducer to perform a sector scan covering the HM plane, to obtain the at least one transverse ultrasound image, which is a sequence of transverse ultrasound images.

14. The method of claim 12, wherein the threshold is determined based on corresponding at least one morphometric parameter of one or more normal individuals.

15. The method of claim 14, wherein the threshold is determined using a machine learning model trained with data of the corresponding at least one morphometric parameter of one or more normal individuals and data of corresponding at least one morphometric parameter of one or more patients confirmed as having obstructive sleep apnea.

16. The method of claim 12, wherein the at least one morphometric parameter is determined using a trained machine learning model based on the at least one transverse ultrasound image or the at least one sagittal ultrasonic image.

17. The method of claim 13, wherein the sector scan covers about 0 to about 15 degrees below and about 0 to about 15 degrees above the HM plane.

18. The system of claim 11, further comprising an automatic ultrasonic scanning system.

19. The system of claim 18, wherein the automatic ultrasonic scanning system is equipped with one or more laser projectors for positioning head and neck of the subject.

* * * * *